US009453847B2

(12) United States Patent
Ruiz et al.

(10) Patent No.: US 9,453,847 B2
(45) Date of Patent: Sep. 27, 2016

(54) MANNOSE RECEPTOR C TYPE 1 (MRC1) CODON OPTIMIZED CELL LINE AND USES THEREOF

(75) Inventors: Juan Ruiz, Acton, MA (US); Marcia Sellos-Moura, West Newbury, MA (US); Michael F. Concino, Bolton, MA (US); Pan Luying, Newton, MA (US); Paolo Martini, Boston, MA (US); Bettina Strack-Logue, Somerville, MA (US); Scott Alderucci, Sutton, MA (US)

(73) Assignee: SHIRE HUMAN GENETIC THERAPIES, INC., Lexington, MA (US)

( * ) Notice: Subject to any disclaimer, the term of this patent is extended or adjusted under 35 U.S.C. 154(b) by 0 days.

(21) Appl. No.: 13/811,122

(22) PCT Filed: Jul. 19, 2011

(86) PCT No.: PCT/US2011/044577
§ 371 (c)(1),
(2), (4) Date: Apr. 8, 2013

(87) PCT Pub. No.: WO2012/012461
PCT Pub. Date: Jan. 26, 2012

(65) Prior Publication Data
US 2013/0195836 A1    Aug. 1, 2013

Related U.S. Application Data

(60) Provisional application No. 61/365,755, filed on Jul. 19, 2010.

(51) Int. Cl.
| | |
|---|---|
| *G01N 33/68* | (2006.01) |
| *A61K 38/47* | (2006.01) |
| *C07K 14/705* | (2006.01) |
| *C12N 9/24* | (2006.01) |
| *C12Q 1/00* | (2006.01) |
| *G06Q 50/22* | (2012.01) |

(52) U.S. Cl.
CPC ........... *G01N 33/6854* (2013.01); *A61K 38/47* (2013.01); *C07K 14/705* (2013.01); *C12N 9/2402* (2013.01); *C12Y 302/01045* (2013.01); *G06Q 50/22* (2013.01)

(58) Field of Classification Search
CPC ............ C12Q 1/00; C12Q 1/34; C12Q 1/68; G01N 33/53; G01N 33/5005; G01N 33/58; G01N 33/68; A61K 38/47
See application file for complete search history.

(56) References Cited

U.S. PATENT DOCUMENTS

| | | |
|---|---|---|
| 4,925,796 A | 5/1990 | Bergh et al. |
| 5,236,838 A | 8/1993 | Rasmussen et al. |
| 5,272,066 A | 12/1993 | Bergh et al. |
| 5,549,892 A | 8/1996 | Friedman et al. |
| 5,929,304 A | 7/1999 | Radin et al. |
| 5,939,279 A | 8/1999 | Smith et al. |
| 6,074,864 A | 6/2000 | Ginns et al. |
| 6,270,989 B1 | 8/2001 | Treco et al. |
| 6,534,300 B1 | 3/2003 | Canfield |
| 6,537,785 B1 | 3/2003 | Canfield |
| 6,642,038 B1 | 11/2003 | Canfield |
| 6,670,165 B2 | 12/2003 | Canfield |
| 6,770,468 B1 | 8/2004 | Canfield |
| 7,138,262 B1 | 11/2006 | Daniel |
| 2002/0025550 A1 | 2/2002 | Canfield |
| 2003/0148460 A1 | 8/2003 | Canfield |
| 2006/0024670 A1 | 2/2006 | Luke et al. |
| 2006/0216722 A1 | 9/2006 | Betsholtz et al. |
| 2007/0031945 A1 | 2/2007 | Daniel |
| 2007/0072175 A1 | 3/2007 | Cooper et al. |
| 2007/0280925 A1 | 12/2007 | Meeker et al. |
| 2011/0027254 A1* | 2/2011 | Daniel et al. ............... 424/94.61 |

FOREIGN PATENT DOCUMENTS

| | | |
|---|---|---|
| CN | 1335505 A | 2/2002 |
| JP | 3-503721 A | 8/1991 |
| JP | 11-318441 A | 11/1999 |
| WO | 9007573 A1 | 7/1990 |
| WO | 9412628 A1 | 6/1994 |
| WO | 9414837 A1 | 7/1994 |
| WO | 9802161 A1 | 1/1998 |
| WO | 9811206 A2 | 3/1998 |
| WO | 9940206 A1 | 8/1999 |
| WO | 9951724 A1 | 10/1999 |
| WO | 9957325 A2 | 11/1999 |
| WO | 9961592 A1 | 12/1999 |

(Continued)

OTHER PUBLICATIONS

Zimran, A. et al. 2007. A pharmacokinetic analysis of a novel enzyme replacement therapy with Gene-Activated human glucocerebrosidase (GA-GCB) in patients with type 1 Gaucher disease. Blood, Cells, Molecules, and Diseases 39:115-118.*
"Shire Human Genetic Therapies. Study of GA-GCB Enzyme Replacement Therapy in Type 1 Gaucher Disease Patients Previously Treated with Imiglucerase" Clinicaltrials.gove (2008).
Aerts et al., "Efficient routing of glucocerebrosidase to lysosomes requires complex oligosaccharide chain formation," Biochemical and Biophysical Research Communications, 1986, vol. 141, No. 2, pp. 452-458.
Ahrens, "Role of target cell glycoproteins in sensitivity to natural killer cell lysis," The Journal of Biological Chemistry, 1993, vol. 268, No. 1, pp. 385-391.
Barton et al., "Therapeutic response to intravenous infusions of glycocerebrosidase in a patient with Gaucher disease," Proc. Natl. Acad. Sci. USA, Mar. 1990, vol. 87, pp. 1913-1916.

(Continued)

*Primary Examiner* — Ruixiang Li
(74) *Attorney, Agent, or Firm* — Troutman Sanders LLP

(57) ABSTRACT

Described herein are isolated nucleic acid molecules comprising nucleotide sequence encoding mannose receptor, C type 1 (MRC1) wherein the 5' region of the nucleotide sequence encoding MRC1 is codon optimized; cells comprising such nucleic acid molecules; and methods of detecting antibody production, e.g., neutralizing antibody production, in a subject being treated for Gaucher disease using such cells.

26 Claims, 16 Drawing Sheets

(56) References Cited

FOREIGN PATENT DOCUMENTS

| WO | 9964587 A1 | 12/1999 |
|---|---|---|
| WO | 0034490 A1 | 6/2000 |
| WO | 0119955 A2 | 3/2001 |
| WO | 0149830 A2 | 7/2001 |
| WO | 2011017177 A1 | 2/2011 |
| WO | 2012012461 A2 | 1/2012 |

OTHER PUBLICATIONS

Berg-Fussman et al., "Human acid b-glucosidase," The Journal of Biological Chemistry, 1993, vol. 268, No. 20, pp. 14861-14866.

Beutler et al., "Failure of Alglucerase Infused into Gaucher Disease Patients to Localize in Marrow Macrophages", Molecular Medicine, vol. 1, No. 3, pp. 320-324 (1995).

Beutler et al., "Polymorphism in the human glucocerebrosidase gene," Genomics, 1992, vol. 12, No. 4, pp. 795-800.

Bijsterbosch et al., "Quantitative analysis of the targeting of mannose-terminal glucocerebrosidase predominant uptake by liver endothelial cells," Eur. J. Biochem., 1996, vol. 237, pp. 344-349.

Bischoff et al., "The effect of 1-deoxymannojirimycin on rat liver a-mannosidases," Biochem. Biophys. Res. Commun., 1984, vol. 125, No. 1, pp. 324-331.

Brumshtein et al., "Characterization of gene-activated human acid-b-glucosidase: crystal structure, glycan composition, and internalization into macrophages," Glycobiology, 2009, vol. 20, No. 1, pp. 24-32.

Burton et al., "Hydrophobic charge induction chromatography: salt independent protein absorption and facile elution whit aqueous buffers" Journal of Chromatography, vol. 814, pp. 71-81 (1998).

Chotai et al., "The uptake of Swainsonine, a specific inhibitor of a-D-mannosidase, into normal human fibroblasts in culture," Journal of Cellular Biochemistry, 1983, vol. 21, pp. 107-117.

Cumming, "Glycosylation of recombinant protein therapeutics: control and functional implications," Glycobiology, 1991, vol. 1, No. 2, pp. 115-130.

Daniel et al., "Effects of the a-mannosidase inhibitors, 1,4-dideoxy-1,4-imino-D-mannitol and Swainsonine, on glycoprotein catabolism in cultured macrophages," Glycoconjugate, 1989, vol. 6, pp. 229-240.

Daniel et al., "Mammalian a-mannosidases—multiple forms but a common purpose," Glycobiology, 1994, vol. 4, No. 5, pp. 551-566.

Dulsat et al., "Gaucher's disease", Drugs of the Future, Prous Science, ES, vol. 34, No. 2, pp. 147-149, (2009).

Elbein et al., "Kifunensine inhibits glycoprotein processing and the function of the modified LDL receptor in endothelial cells," Archives of Biochemistry and Biophysics, 1991, vol. 288, No. 1, pp. 177-184.

Elbein et al., "Kifunensine, a potent inhibitor of the glycoprotein processing mannosidase I," The Journal of Biological Chemistry, 1990, vol. 265, No. 26, pp. 15599-15605.

Elbein, "Glycosidase inhibitors: inhibitors of N-linked oligosaccharide processing," The FASEB Journal, 1991, vol. 5, pp. 3055-3063.

Erickson et al., "Biosynthesis of the lysosomal enzyme glucocerebrosidase," The Journal of Biological Chemistry, 1985, vol. 260, No. 26, pp. 14319-14324.

Extended European Search Report from EP Application Serial No. 10182992.7 mailed Apr. 29, 2011.

Extended European Search Report from EP Application Serial No. 10806936 dated Mar. 27, 2013.

Fleet et al., "Design synthesis and prelimiary evaluation of a potent a-mannosidase inhibitor: 1,4-dideoxy-1,4-imino-D-mannitol," J. Chem. Soc. Chem. Commun., 1984, pp. 1240-1241.

Friedman et al., "A comparison of the pharmacological properties of carbohydrate remodeled recombinant and placental-derived b-glucocerebrosidase: implications for clinical efficacy in treatment of Gaucher disease," Blood, 1999, vol. 93, pp. 2807-2816.

Furbish et al., "Uptake and distribution of placental glucocerebrosidase in rat hepatic cells and effects of sequential deglycosylation," Biochimica et Biophysica Acta, 1981, vol. 673, pp. 425-434.

Giraldo et al., "Safety with Velaglucerasein Two Girls Previously Treated with Imiglucerase" Spanish Gaucher Disease Foundation, P20 (presented at the 9th annual EWGGD, Cologne, Germany) (2010).

Gonzalez et al., "Identification, expression, and characterization of a cDNA encoding human endoplasmic reticulum mannosidase I, the enzyme that catalyzes the first mannose trimming step in mammalian Asn-linked oligosaccharide biosynthesis," J. Biol. Chem., 1999, vol. 274, No. 30, pp. 21375-21386.

Grabowski et al., "Enzyme Thearpy in Type 1 Gaucher Disease: Comparative Efficacy of Mannose-terminated Glucocerebrosidase from Natural and Recombinant Sources", Annals of Internal Medicine, vol. 122, No. 1, pp. 33-39 (1995).

Guerrier et al., "New method for the selctive capture of antibodies under physiolgical conditions" Bioseparation, vol. 9, pp. 211-221 (2000).

International Preliminary Report on Patentability and Written Opinion from corresponding International Application Serial No. PCT/US2010/043586 dated Nov. 22, 2010.

Marcus et al., "Glucosidase and mannosidase inhibitors mediate increased secretion of mutant al antitrypsin Z," The Journal of Biological Chemistry, 2000, vol. 275, No. 3, pp. 1987-1992.

Martin et al., "Glycosylation and processing of high levels of active human glucocerebrosidase in invertebrate cells using a baculovirus expression vector," DNA, 1988, vol. 7, No. 2, pp. 99-106.

Mistry et al., "Therapeutic delivery of proteins to macrophages: implications for treatment of Gaucher's disease", The Lancet, vol. 348, No. 9041, pp. 1555-1559 (1996).

Moremen et al., "Glycosidases of the asparagine-linked oligosaccharide processing pathway," Glycobiology, 1994, vol. 4, No. 2, pp. 113-125.

Palamarczyk et al., "1,4-Dideoxy-1,4-imino-D-mannitol inhibits glycoprotein processing and mannosidase," Archives of Biochemistry and Biophysics, 1985, vol. 243, No. 1, pp. 35-45.

Pastores et al. "Therapreutic Goals in the Treatement of Gaucher Disease" Seminars in Hematology 41 (suppl5):4-14. 2004.

Peterson et al., "Comparison of in vitro cellular uptake of velaglucerase alfa to that of imiclucerase" Department of Research and Development, Shire Genetic Therapies, P34 (presented at the 9th annual EWGGD, Cologne, Germany) (2010).

Reinke et al., "Efficacy and Tolerability of Velaglucerase Alfa in Treament of 7 patients with Type I Gaucher Disease—First Observations" Children's Hospital, Gutenberg—University of Mainz, P38 (presented at the 9th annual EWGGD, Cologne, Germany) (2010).

Rosenberg et al., "Immunosurveillance of alglucerase enzyme therapy for Gaucher patients: Induction of humoral tolerance in seroconverted patients after repeat administration", Blood, vol. 93, pp. 2081-2088 (1999).

Rudd et al., "Diversification of the IgG molecule by oligosaccharides," Molecular Immunology, 1991, vol. 28, No. 12, pp. 1369-1378.

Sato et al., "Binding, internalization, and degradation of mannose-terminated glucocerebrosidase my macrophages," J. Clin. Invest., 1993, vol. 91, pp. 1909-1917.

Schutzbach et al., "Calcium ion activation of rabbit liver a1,2-mannosidase", J. Biol. Chem., 1990, vol. 265, No. 5, pp. 2546-2549.

Shah et al., "Comparison of kifunensine and 1-deoxymannojirimycin binding to class I and II a-mannosidases demonstrates different saccharide distortions in inverting and retaining catalytic mechanisms," Biochemistry, 2003, vol. 42, pp. 13812-13816.

Takahashi et al., "Enzyme therapy in Gaucher disease type 2: an autopsy case," Tohoku J. Exp. Med., 1998, vol. 186, pp. 143-149.

Takasaki et al., "Structure of the N-asparagine-linked oligosaccharide units of human placental b-glucocerebrosidase," The Journal of Biological Chemistry, 1984, vol. 259, No. 16, pp. 10112-10117.

(56) References Cited

OTHER PUBLICATIONS

Trembley et al., "Characterization of a cDNA encoding a novel human golgi α1,2-mannosidase (IC) involved in N-glycan biosynthesis," The Journal of Biological Chemistry, 2000, vol. 275, No. 41, pp. 31655-31660.
Tropea et al., "Mannostatin A, a new glycoprotein-processing inhibitor", Biochemistry, 1990, vol. 29, No. 43, pp. 10062-10069.
Tulsiani et al., "Swainsonine inhibits the biosynthesis of complex glycoproteins by inhibition of golgi mannosidase II," The Journal of Biological Chemistry, 1982, vol. 257, No. 14, pp. 7936-7939.
Van Weely et al., "Function of oligosaccharide modification in glucocerebrosidase, a membrane-associated lysosomal hydrolase," Eur. J. Biochem., 190, vol. 191, pp. 669-677.
Wadhwa et al., "Strategies for detection, measurement and characterization of unwanted antibodies induced by therapeutic biologicals"Journal of Immun. vol. 278, No. 1-2, pp. 1-17 (2003).
Wang et al., "Neutralizing antibodies to therapeutic enzymes: considerations fro testing, prevention and treatment" Nature Biotechnology, vol. 26, No. 8 pp. 901-908 (2008).
Weng et al., "Demonstration that a kifunensine-resistant a-mannosidase with a unique processing action on N-linked oligosaccharides occurs in rat liver endoplasmic reticulum and various cultured cells," The Journal of Biological Chemistry, 1993, vol. 268, No. 34, pp. 25656-25663.
Winchester et al., "The structural basis of the inhibition of human a-mannosidases by azafuranose analogues of mannose", Biochem. J., 1993, vol. 290, pp. 743-749.
Wustman et al. "Pharmacological chaperone therapy for Gaucher disease: Mechansim of action, a survey of responsive mutations and phase I clinical trial results." Molecular Genetics and Metabolism vol. 93 pp. S14-S46 (2008).
Zimran et al., "Enzyme replacement therapy in type 1 and type 3 Gaucher's desease," The Lancet, 1995, vol. 345, pp. 451-452.
Database EMBL [online] "H.sapriens mRNA for macrophage mannose receptor" retrieved from EPI accession No. EM_STD:X55635 database accession No. X55635. Apr. 15, 1992.
Extended European Search Report from EP Application Serial No. 11810304.3 dated Jan. 31, 2014.
Genzyme Corporation. "Cerezyme (imiglucerase) Injection, Powder, Lyophilized, for Solution." DailyMed Archived Drug Labels (online), Feb. 1, 2006, p. 1-6.
Richards et al. "Antibody Response in Patients with Gaucher Disease After Repeated Infusion with Macrophage-Targeted Glucocerebrosidase" Blood, 1993, vol. 82, No. 5, pp. 1402-1409.
Wang et al. "Neutralizing antibodies to therapeutic enzymes: considerations for testing, prevention and treatment", Nature Biotechnology, vol. 26, No. 8., Aug. 1, 2008, pp. 901-908.
Xiao et al., "Effectiveness of enzyme replacement therapy to patients with Gaucher Disease," China Chold Blood, 2004, vol. 9, No. 5. pp. 197-200.
EM_EST:DV041364; DAY 10_01_L11.x1 FH DAY 10 Mus musculus cDNA clone DAY 10_01-L11 similar to Mannose receptor C type 1, mRNA sequence; created Sep. 28, 2005.
GenBank Direct Submission DQ663787, "*Homo sapiens* mannose receptor mRNA, complete cds" Retrieved from the internet Feb. 7, 2012 from http://www.ncbi.nlm.nih.gov/nuccore/DQ663787.
Supplementary European Search Report issued on Jan. 16, 2014 in European Application No. 11 810 304.3, which corresponds to the present application.
International Search Report dated Mar. 2, 2012 issued in PCT/US2011/044577, which corresponds to the present application.
EPO Communication issued on Dec. 2, 2014 in European Application No. 11 810 304.3, which corresponds to the present application.
EPO Communication issued on Jun. 25, 2015 in European Application No. 11 810 304.3, which corresponds to the present application.
Burgess-Brown et al., "Codon optimization can improve expression of human genes in Escherichia coli: A multi-gene study," Protein Expression and Purification 59: 94-102, 2008.
Ezekowitz et al., "Molecular characterization of the human macrophage mannose receptor: Demonstration of multiple aarbohydrate recognition-like domains and phagocytosis of yeasts in Cos-1 Cells," J. Exp. Med. 172: 1785-1794, 1990.

* cited by examiner

SEQUENCE LISTING

```
<160> NUMBER OF SEQ ID NOS: 8

<210> SEQ ID NO 1
<211> LENGTH: 4371
<212> TYPE: DNA
<213> ORGANISM: Homo sapiens

<400> SEQUENCE: 1
atgaggctac cctgctcct ggttttttgcc tctgtcattc cgggtgctgt tctcctactg      60
gacaccaggc aatttttaat ctataatgaa gatcacaagc gctgcgtgga tgcagtgagt     120
```

```
cccagtgccg tccaaaccgc agcttgcaac caggatgccg aatcacagaa attccgatgg    180
gtgtccgaat ctcagattat gagtgttgca tttaaattat gcctgggagt gccatcaaaa    240
acagactggg ttgctatcac tctctatgcc tgtgactcaa aaagtgaatt tcagaaatgg    300
gagtgcaaaa atgacacact tttggggatc aaaggagaag atttatttt taactacggc     360 aacagacaag aaaagaatat tatgctctac aagggatcgg gtttatggag caggtggaag    420
atctatggaa ccacagacaa tctgtgctcc agaggttatg aagccatgta tacgctacta    480
ggcaatgcca atggagcaac ctgtgcattc ccgttcaagt ttgaaaacaa gtggtacgca    540
gattgcacga gtgctgggcg gtcggatgga tggctctggt gcggaaccac tactgactat    600
gacacagaca agctatttgg atattgtcca ttgaaatttg agggcagtga agcttatgg     660 aataaagacc cgctgaccag cgtttcctac cagataaact ccaaatccgc tttaacgtgg    720
caccaagcga ggaaaagctg ccaacaacag aacgctgagc tcctgagcat cacagagata    780
catgagcaaa catacctgac aggattaacc agttccttga cctcaggact ctggattgga    840
cttaacagtc tgagcttcaa cagcggttgg cagtggagtg accgcagtcc tttccgatat    900
ttgaactggt taccaggaag tccatcagct gaacctggaa aaagctgtgt gtcactaaat    960
cctggaaaaa atgctaaatg ggaaaatctg gaatgtgttc agaaactggg ctatatttgc    1020
aaaaagggca acaccacttt aaattctttt gttattccct cagaaagtga tgtgcctact    1080
cactgtccta gtcagtggtg gccgtatgcc ggtcactgtt acaagattca cagagatgag    1140
aaaaaaatcc agagggatgc tctgaccacc tgcaggaagg aaggcggtga cctcacaagt    1200
atccacacca tcgaggaatt ggactttatt atctcccagc taggatatga gccaaatgac    1260
gaattgtgga tcggcttaaa tgacattaag attcaaatgt actttgagtg gagtgatggg    1320 accccctgtaa cgtttaccaa atggcttcgt ggagaaccaa gccatgaaaa caacagacag    1380
gaggattgtg tggtgatgaa aggcaaggat gggtactggg cagatcgggg ctgtgagtgg    1440
cctcttggct acatctgcaa gatgaaatca cgaagccaag gtccagaaat agtggaagtc    1500
gaaaaaggct gcaggaaagg ctggaaaaaa catcacttttt actgctatat gattggacat    1560
acgctttcaa catttgcaga agcaaaccaa acctgtaata atgagaatgc ttatttaaca    1620
actattgaag acagatatga acaagccttc ctgactagtt tcgttggctt aaggcctgaa    1680
aaatatttct ggacaggact ttcagatata caaaccaaag gacttttca gtggaccatc    1740 gaggaagagg ttcggttcac ccactggaat tcagatatgc cagggcgaaa gccagggtgt    1800
gttgccatga gaaccgggat tgcaggggggc ttatgggatg ttttgaaatg tgatgaaaag    1860
gcaaaatttg tgtgcaagca ctgggcagaa ggagtaaccc acccaccgaa gcccacgacg    1920
actcccgaac ccaaatgtcc ggaggattgg gcgccagca gtagaacaag cttgtgtttc    1980
aagctgtatg caaaaggaaa acatgagaag aaaacgtggt ttgaatctcg agattttttgt    2040 cgagctctgg gtggagactt agctagcatc aataacaaag aggaacagca acaatatgg     2100 cgattaataa cagctagtgg aagctaccac aaactgttt ggttgggatt gacatatgga    2160
agcccttcag aaggttttac ttggagtgat ggttctcctg tttcatatga aaactgggct    2220 tatgagaac ctaataatta tcaaaatgtt gaatactgtg gtgagctgaa aggtgaccct    2280
actatgtctt ggaatgatat taattgtgaa caccttaaca actggatttg ccagatacaa    2340
aaaggacaaa caccaaaacc tgagccaaca ccagctcctc aagacaatcc accagttact    2400
gaagatgggt gggttattta caaagactac cagtattatt tcagcaaaga gaaggaaacc    2460
```

```
atggacaatg cgcgagcgtt ttgcaagagg aatttggtg atcttgtttc tattcaaagt    2520
gaaagtgaaa agaagtttct atggaaatat gtaaacagaa atgatgcaca gtctgcatat    2580
tttattggtt tattgatcag cttggataaa aagtttgctt ggatggatgg aagcaaagtg    2640
gattacgtgt cttgggccac aggtgaaccc aattttgcaa atgaagatga aaactgtgtg    2700
accatgtatt caaattcagg ttttggaat gacattaact gtggctatcc aaacgccttc    2760
atttgccagc gacataacag tagtatcaat gctaccacag ttatgcctac catgccctcg    2820
gtcccatcag ggtgcaagga aggttggaat ttctacagca acaagtgttt caaaatcttt    2880
ggatttatgg aagaagaaag aaaaaattgg caagaggcac gaaaagcttg tataggcttt    2940
ggagggaatc tggtctccat acaaaatgaa aaagagcaag catttcttac ctatcacatg    3000
aaggactcca ctttcagtgc ctggactggg ctgaatgatg tcaattcaga acacacgttc    3060
ctttggacgg atggacgagg agtccattac acaaactggg ggaaaggtta ccctggtgga    3120
agaagaagca gtctttctta tgaagatgct gactgtgttg ttattattgg aggtgcatca    3180
aatgaagcag gaaaatggat ggatgatacc tgcgacagta acgaggcta catatgccag    3240 acacgatccg acccttcctt gactaatcct ccagcaacga ttcaaacaga tggctttgtt    3300
aaatatggca aaagcagcta ttcactcatg agacaaaaat ttcaatggca tgaagcggag    3360
acatactgca agcttcacaa tttcccttata gccagcattc tggatcccta cagtaatgca    3420
tttgcgtggc tgcagatgga acatctaat gaacgtgtgt ggatcgccct gaacagtaac    3480
ttgactgata atcaatacac ttggactgat aagtggaggg tgaggtacac taactgggct    3540
gctgatgagc ccaaattgaa atcagcatgt gtttatctgg atcttgatgg ctactggaag    3600
acagcacatt gcaatgaaag tttttacttt ctctgtaaaa gatcagatga aatccctgct    3660
actgaacccc cacaactgcc tggcagatgc ccggagtcag atcacacagc atggattcct    3720
ttccatggtc actgttacta tattgagtcc tcatatacaa gaaactgggg ccaagcttct    3780
ctggaatgtc ttcgaatggg ttcctctctg gtttccattg aaagtgctgc agaatccagt    3840
tttctgtcat atcgggttga gccacttaaa agtaaaacca atttttggat aggattgttc    3900
agaaatgttg aagggacgtg gctgtggata aataacagtc cggtctcctt tgtcaactgg    3960
aacacaggag atccctctgg tgaacggaat gattgtgtag ctttacatgc gtcttctggg    4020
ttttggagta atattcactg ttcatcctac aaaggatata tttgtaaaag accaaaaatt    4080
attgatgcta aacctactca tgaattactt acaacaaaag ctgacacaag gaagatggac    4140
ccttctaaac cgtcttccaa cgtggccgga gtagtcatca ttgtgatcct cctgattttta    4200 acgggtgctg gccttgccgc ctatttcttt tataagaaaa gacgtgtgca cctacctcaa    4260
gagggcgcct ttgaaaacac tctgtatttt aacagtcagt caagcccagg aactagtgat    4320
atgaaagatc tcgtgggcaa tattgaacag aatgaacact cggtcatcta g             4371
```

<210> SEQ ID NO 2
<211> LENGTH: 2067
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgagactgc cctgctgct ggtgttcgcc agcgtgatcc ccggcgccgt gctgctgctg     60
gacaccagac agttcctgat ctacaacgag gaccacaaga gatgcgtgga cgccgtgagc    120
```

```
cccagcgccg tgcagaccgc cgcctgcaac caggacgccg agagccagaa gttcagatgg    180
gtgagcgaga gccagatcat gagcgtggcc ttcaagctgt gcctgggcgt gcccagcaag    240
accgactggg tggccatcac cctgtacgcc tgcgacagca gagcgagtt ccagaagtgg     300 gagtgcaaga cgacaccct gctgggcatc aagggcgagg acctgttctt caactacggc    360
aacagacagg agaagaacat catgctgtac aagggcagcg gcctgtggag cagatggaag    420
atctacggca ccaccgacaa cctgtgcagc agaggctacg aggccatgta cacctgctg     480 ggcaacgcca acggcgccac ctgcgccttc cccttcaagt tcgagaacaa gtggtacgcc    540
gactgcacca gcgccggcag aagcgacggc tggctgtggt gcggcaccac caccgactac    600
gacaccgaca agctgttcgg ctactgcccc ctgaagttcg agggcagcga gagcctgtgg    660
aacaaggacc ccctgaccag cgtgagctac cagatcaaca gcaagagcgc cctgagctgg    720
caccaggcca gaaagagctg ccagcagcag aacgccgagc tgctgagcat caccgagatc    780
cacgagcaga cctacctgac cggcctgacc agcagcctga ccagcggcct gtggatcggc    840
ctgaacagcc tgagcttcaa cagcggctgg cagtggagcg acagaagccc cttcagatac    900
ctgaactggc tgcccggcag ccccagcgcc gagcccggca agagctgcgt gagcctgaac    960
cccggcaaga cgccaagtg ggagaacctg gagtgcgtgc agaagctggg ctacatctgc    1020
aagaagggca acaccaccct gaacagcttc gtgatcccca gcgagagcga cgtgcccacc    1080
cactgcccca gccagtggtg gcctacgcc ggccactgct acaagatcca cagagacgag    1140
aagaagatcc agagagacgc cctgaccacc tgcagaaagg agggcggcga cctggccagc    1200
atccacacca tcgaggagtt cgacttcatc atcagccagc tgggctacga gcccaacgac    1260
gagctgtgga tcggcctgaa cgacatcaag atccagatgt acttcgagtg gagcgacggc    1320 accccgtga ccttcaccaa gtggctgaga ggcgagccca gccacgagaa caacagacag    1380
gaggactgcg tggtgatgaa gggcaaggac ggctactggg ccgacagagg ctgcgagtgg    1440 ccctgggct acatctgcaa gatgaagagc agaagccagg gccccgagat cgtggaggtg    1500
gagaagggct gcagaaaggg ctggaagaag caccacttct actgctacat gatcggccac    1560
accctgagca ccttcgccga ggccaaccag acctgcaaca acgagaacgc ctacctgacc    1620
accatcgagg acagatacga gcaggccttc ctgaccagct tcgtgggcct gagacccgag    1680
aagtacttct ggaccggcct gagcgacatc cagaccaagg gcaccttcca gtggaccatc    1740
gaggaggagg tgagattcac ccactggaac agcgacatgc ccggcagaaa gcccggctgc    1800
gtggccatga aaccggcat cgccggcggc ctgtgggacg tgctgaagtg cgacgagaag    1860
gccaagttcg tgtgcaagca ctgggccgag ggcgtgaccc accccccaa gcccaccacc    1920 acccccgagc caagtgccc cgaggactgg ggcgccagca gcagaaccag cctgtgcttc    1980
aagctgtacg ccaagggcaa gatcgagaag aagacctggt tcgagagcag agacttctgc    2040
agagccctgg gcggcgacct ggctagc                                        2067
```

<210> SEQ ID NO 3
<211> LENGTH: 2067
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgagactgc ccctgctgct ggtgttcgcc agcgtgatcc ccggcgccgt gctgctgctg    60
```

| | |
|---|---|
| gacaccagac agttcctgat ctacaacgag gaccacaaga gatgcgtgga cgccgtgagc | 120 |
| cccagcgccg tgcagaccgc cgcctgtaat caagacgcag agagccagaa gttcagatgg | 180 |
| gtgagcgaga gccagatcat gagcgtggcc ttcaagctgt gcctgggcgt gcccagcaag | 240 |
| accgactggg tggccatcac cctgtacgcc tgcgacagca gagcgagtt ccagaagtgg | 300 |
| gagtgcaaga cgacaccct gctgggcatc aagggcgagg acctgttctt caactacggc | 360 |
| aacagacagg agaagaacat catgctgtac aagggcagcg gcctgtggag cagatggaag | 420 |
| atctacggca ccaccgacaa cctgtgcagc agaggctacg aggccatgta caccctgctg | 480 |
| ggcaacgcca cggcgccac ctgcgccttc cccttcaagt tcgagaacaa gtggtacgcc | 540 |
| gactgcacca gcgccggcag aagcgacggc tggctgtggt gcggcaccac caccgactac | 600 |
| gacaccgaca gctgttcgg ctactgcccc ctgaagttcg agggcagcga gagcctgtgg | 660 |
| aacaaggacc ccctgaccag cgtgagctac cagatcaaca gcaagagcgc cctgacctgg | 720 |
| caccaggcca gaaagagctg ccagcagcag aacgccgagc tgctgagcat caccgagatc | 780 |
| cacgagcaga cctacctgac cggcctgacc agcagcctga ccagcggcct gtggatcggc | 840 |
| ctgaacagcc tgagcttcaa cagcggctgg cagtggagcg acagaagccc cttcagatac | 900 |
| ctgaactggc tgcccggcag ccccagcgcc gagcccggca gagctgcgt gagcctgaac | 960 |
| cccggcaaga cgccaagtg ggagaacctg gagtgcgtgc agaagctggg ctacatctgc | 1020 |
| aagaagggca acaccaccct gaacagcttc gtgatcccca gcgagagcga cgtgcccacc | 1080 |
| cactgccca gccagtggtg gccctacgcc ggccactgct acaagatcca cagagacgag | 1140 |
| aagaagatcc agagagacgc cctgaccacc tgcagaaagg agggcggcga cctgaccagc | 1200 |
| atccacacca tcgaggagct ggacttcatc atcagccagc tgggctacga gcccaacgac | 1260 |
| gagctgtgga tcgccctgaa cgacatcaag atccagatgt acttcgagtg gagcgacggc | 1320 |
| accccgtga ccttcaccaa gtggctgaga ggcgagccca gccacgagaa caacagacag | 1380 |
| gaggactgcg tggtgatgaa gggcaaggac ggctactggg ccgacagagg ctgcgagtgg | 1440 |
| cccctgggct acatctgcaa gatgaagagc agaagccagg gccccgagat cgtggaggtg | 1500 |
| gagaagggct gcagaaaggg ctggaagaag caccacttct actgctacat gatcggccac | 1560 |
| accctgagca ccttcgccga ggccaaccag acctgcaaca acgagaacgc ctacctgacc | 1620 |
| accatcgagg acagatacga gcaggccttc ctgaccagct cgtgggcct gagacccgag | 1680 |
| aagtacttct ggaccggcct gagcgacatc cagaccaagg gcaccttcca gtggaccatc | 1740 |
| gaggaggagg tgagattcac ccactggaac agcgacatgc ccggcagaaa gcccggctgc | 1800 |
| gtggccatga gaaccggcat cgccggcggc ctgtgggacg tgctgaagtg cgacgagaag | 1860 |
| gccaagttcg tgtgcaagca ctgggccgag ggcgtgaccc accccccaa gcccaccacc | 1920 |
| accccgagc ccaagtgccc cgaggactgg ggcgccagca gcagaaccag cctgtgcttc | 1980 |
| aagctgtacg ccaagggcaa gcacgagaag aagacctggt tcgagagcag agacttctgc | 2040 |
| agagccctgg gcggcgacct ggctagc | 2067 |

<210> SEQ ID NO 4
<211> LENGTH: 1456
<212> TYPE: PRT
<213> ORGANISM: Homo sapiens

<400> SEQUENCE: 4

Met Arg Leu Pro Leu Leu Leu Val Phe Ala Ser Val Ile Pro Gly Ala
1               5                   10                  15

```
Val Leu Leu Leu Asp Thr Arg Gln Phe Leu Ile Tyr Asn Glu Asp His
                20                  25                  30

Lys Arg Cys Val Asp Ala Val Ser Pro Ser Ala Val Gln Thr Ala Ala
         35                  40                  45

Cys Asn Gln Asp Ala Glu Ser Gln Lys Phe Arg Trp Val Ser Glu Ser
     50                  55                  60

Gln Ile Met Ser Val Ala Phe Lys Leu Cys Leu Gly Val Pro Ser Lys
 65                  70                  75                  80

Thr Asp Trp Val Ala Ile Thr Leu Tyr Ala Cys Asp Ser Lys Ser Glu
                 85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
    130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
    210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
    290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
        355                 360                 365

Tyr Ala Gly His Cys Tyr Lys Ile His Arg Asp Glu Lys Lys Ile Gln
    370                 375                 380

Arg Asp Ala Leu Thr Thr Cys Arg Lys Glu Gly Gly Asp Leu Thr Ser
385                 390                 395                 400

Ile His Thr Ile Glu Glu Leu Asp Phe Ile Ile Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
```

-continued

```
              435                 440                 445
Leu Arg Gly Glu Pro Ser His Glu Asn Asn Arg Gln Glu Asp Cys Val
450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                    485                 490                 495

Ile Val Glu Val Glu Lys Gly Cys Arg Lys Gly Trp Lys Lys His His
                500                 505                 510

Phe Tyr Cys Tyr Met Ile Gly His Thr Leu Ser Thr Phe Ala Glu Ala
                515                 520                 525

Asn Gln Thr Cys Asn Asn Glu Asn Ala Tyr Leu Thr Thr Ile Glu Asp
530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                    565                 570                 575

Gln Trp Thr Ile Glu Glu Val Arg Phe Thr His Trp Asn Ser Asp
                580                 585                 590

Met Pro Gly Arg Lys Pro Gly Cys Val Ala Met Arg Thr Gly Ile Ala
                595                 600                 605

Gly Gly Leu Trp Asp Val Leu Lys Cys Asp Glu Lys Ala Lys Phe Val
610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                    645                 650                 655

Ser Leu Cys Phe Lys Leu Tyr Ala Lys Gly Lys His Glu Lys Lys Thr
                660                 665                 670

Trp Phe Glu Ser Arg Asp Phe Cys Arg Ala Leu Gly Gly Asp Leu Ala
                675                 680                 685

Ser Ile Asn Asn Lys Glu Glu Gln Gln Thr Ile Trp Arg Leu Ile Thr
690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                    725                 730                 735

Glu Asn Trp Ala Tyr Gly Glu Pro Asn Asn Tyr Gln Asn Val Glu Tyr
                740                 745                 750

Cys Gly Glu Leu Lys Gly Asp Pro Thr Met Ser Trp Asn Asp Ile Asn
                755                 760                 765

Cys Glu His Leu Asn Asn Trp Ile Cys Gln Ile Gln Lys Gly Gln Thr
                770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
                    805                 810                 815

Glu Lys Glu Thr Met Asp Asn Ala Arg Ala Phe Cys Lys Arg Asn Phe
                820                 825                 830

Gly Asp Leu Val Ser Ile Gln Ser Glu Ser Glu Lys Lys Phe Leu Trp
                835                 840                 845

Lys Tyr Val Asn Arg Asn Asp Ala Gln Ser Ala Tyr Phe Ile Gly Leu
850                 855                 860
```

-continued

```
Leu Ile Ser Leu Asp Lys Lys Phe Ala Trp Met Asp Gly Ser Lys Val
865                 870                 875                 880

Asp Tyr Val Ser Trp Ala Thr Gly Glu Pro Asn Phe Ala Asn Glu Asp
                885                 890                 895

Glu Asn Cys Val Thr Met Tyr Ser Asn Ser Gly Phe Trp Asn Asp Ile
                900                 905                 910

Asn Cys Gly Tyr Pro Asn Ala Phe Ile Cys Gln Arg His Asn Ser Ser
                915                 920                 925

Ile Asn Ala Thr Thr Val Met Pro Thr Met Pro Ser Val Pro Ser Gly
930                 935                 940

Cys Lys Glu Gly Trp Asn Phe Tyr Ser Asn Lys Cys Phe Lys Ile Phe
945                 950                 955                 960

Gly Phe Met Glu Glu Glu Arg Lys Asn Trp Gln Glu Ala Arg Lys Ala
                965                 970                 975

Cys Ile Gly Phe Gly Gly Asn Leu Val Ser Ile Gln Asn Glu Lys Glu
                980                 985                 990

Gln Ala Phe Leu Thr Tyr His Met Lys Asp Ser Thr Phe Ser Ala Trp
                995                 1000                1005

Thr Gly Leu Asn Asp Val Asn Ser Glu His Thr Phe Leu Trp Thr
    1010                1015                1020

Asp Gly Arg Gly Val His Tyr Thr Asn Trp Gly Lys Gly Tyr Pro
    1025                1030                1035

Gly Gly Arg Arg Ser Ser Leu Ser Tyr Glu Asp Ala Asp Cys Val
    1040                1045                1050

Val Ile Ile Gly Gly Ala Ser Asn Glu Ala Gly Lys Trp Met Asp
    1055                1060                1065

Asp Thr Cys Asp Ser Lys Arg Gly Tyr Ile Cys Gln Thr Arg Ser
    1070                1075                1080

Asp Pro Ser Leu Thr Asn Pro Pro Ala Thr Ile Gln Thr Asp Gly
    1085                1090                1095

Phe Val Lys Tyr Gly Lys Ser Ser Tyr Ser Leu Met Arg Gln Lys
    1100                1105                1110

Phe Gln Trp His Glu Ala Glu Thr Tyr Cys Lys Leu His Asn Ser
    1115                1120                1125

Leu Ile Ala Ser Ile Leu Asp Pro Tyr Ser Asn Ala Phe Ala Trp
    1130                1135                1140

Leu Gln Met Glu Thr Ser Asn Glu Arg Val Trp Ile Ala Leu Asn
    1145                1150                1155

Ser Asn Leu Thr Asp Asn Gln Tyr Thr Trp Thr Asp Lys Trp Arg
    1160                1165                1170

Val Arg Tyr Thr Asn Trp Ala Ala Asp Glu Pro Lys Leu Lys Ser
    1175                1180                1185

Ala Cys Val Tyr Leu Asp Leu Asp Gly Tyr Trp Lys Thr Ala His
    1190                1195                1200

Cys Asn Glu Ser Phe Tyr Phe Leu Cys Lys Arg Ser Asp Glu Ile
    1205                1210                1215

Pro Ala Thr Glu Pro Pro Gln Leu Pro Gly Arg Cys Pro Glu Ser
    1220                1225                1230

Asp His Thr Ala Trp Ile Pro Phe His Gly His Cys Tyr Tyr Ile
    1235                1240                1245

Glu Ser Ser Tyr Thr Arg Asn Trp Gly Gln Ala Ser Leu Glu Cys
    1250                1255                1260
```

```
Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
    1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttacgcgtcc accatgaggc taccctgct c                                    31

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttaattaact agatgaccga gtgt                                           24

<210> SEQ ID NO 7
<211> LENGTH: 2067
<212> TYPE: DNA
<213> ORGANISM: Artificial Sequence
<220> FEATURE:
<223> OTHER INFORMATION: Description of Artificial Sequence: Synthetic
      Consensus polynucleotide

<400> SEQUENCE: 7
atgagactgc ccctgctgct ggtgttcgcc agcgtgatcc ccggcgccgt gctgctgctg      60
gacaccagac agttcctgat ctacaacgag gaccacaaga gatgcgtgga cgccgtgagc     120
```

```
cccagcgccg tgcagaccgc cgcctgcaac caggacgccg agagccagaa gttcagatgg    180
gtgagcgaga gccagatcat gagcgtggcc ttcaagctgt gcctgggcgt gcccagcaag    240
accgactggg tggccatcac cctgtacgcc tgcgacagca agagcgagtt ccagaagtgg    300
gagtgcaaga acgacaccct gctgggcatc aagggcgagg acctgttctt caactacggc    360
aacagacagg agaagaacat catgctgtac aagggcagcg gcctgtggag cagatggaag    420
atctacggca ccaccgacaa cctgtgcagc agaggctacg aggccatgta caccctgctg    480
ggcaacgcca acggcgccac ctgcgccttc cccttcaagt tcgagaacaa gtggtacgcc    540
gactgcacca cgcgccggca agcgacggc tggctgtggt cggcaccac caccgactac    600 gacaccgaca agctgttcgg ctactgcccc ctgaagttcg agggcagcga gagcctgtgg    660
aacaaggacc ccctgaccag cgtgagctac cagatcaaca gcaagagcgc cctgacctgg    720
caccaggcca gaaagagctg ccagcagcag aacgccgagc tgctgagcat caccgagatc    780
cacgagcaga cctacctgac cggcctgacc agcagcctga ccagcggcct gtggatcggc    840
ctgaacagcc tgagcttcaa cagcggctgg cagtggagcg acagaagccc cttcagatac    900
ctgaactggt gcccggcag ccccagcgcc gagcccggca gagctgcgt gagcctgaac    960 cccggcaaga cgccaagtg ggagaacctg gagtgcgtgc agaagctggg ctacatctgc    1020
aagaagggca caccaccct gaacagcttc gtgatcccca gcgagagcga cgtgcccacc    1080
cactgcccca gccagtggtg gcctacgcc ggccactgct acaagatcca cagagacgag    1140
aagaagatcc agagagacgc cctgaccacc tgcagaaagg agggcggcga cctgaccagc    1200
atccacacca tcgaggagtt ggacttcatc atcagccagc tgggctacga gcccaacgac    1260
gagctgtgga tcggcctgaa cgacatcaag atccagatgt acttcgagtg gagcgacggc    1320 accccccgtga ccttcaccaa gtggctgaga ggcgagccca gccacgagaa caacagacag    1380
gaggactgcg tggtgatgaa gggcaaggac ggctactggg ccgacagagg ctgcgagtgg    1440
cccctgggct acatctgcaa gatgaagagc agaagccagg cccccgagat cgtggaggtg    1500
gagaagggct gcagaaaggg ctggaagaag caccacttct actgctacat gatcggccac    1560
accctgagca ccttcgccga ggccaaccag acctgcaaca cgagaacgc ctacctgacc    1620 accatcgagg acagatacga gcaggccttc ctgaccagct tcgtgggcct gagacccgag    1680
aagtacttct ggaccggcct gagcgacatc cagaccaagg gcaccttcca gtggaccatc    1740
gaggaggagg tgagattcac ccactggaac agcgacatgc ccggcagaaa gcccggctgc    1800
gtggccatga gaaccggcat cgccggcggc ctgtgggacg tgctgaagtg cgacgagaag    1860
gccaagttcg tgtgcaagca ctgggccgag ggcgtgaccc accccccaa gccaccacc    1920 accccgagc caagtgccc cgaggactgg ggcgccagca gcagaaccag cctgtgcttc    1980
aagctgtacg ccaagggcaa gcacgagaag aagacctggt cgagagcag agacttctgc    2040 agagccctgg gcggcgacct ggctagc    2067
```

<210> SEQ ID NO 8
<211> LENGTH: 2067
<212> TYPE: DNA
<213> ORGANISM: Homo sapiens

<400> SEQUENCE: 8

```
atgaggctac ccctgctcct ggttttgcc tctgtcattc cgggtgctgt tctcctactg     60
gacaccaggc aatttttaat ctataatgaa gatcacaagc gctgcgtgga tgcagtgagt    120
```

```
cccagtgccg tccaaaccgc agcttgcaac caggatgccg aatcacagaa attccgatgg    180
gtgtccgaat ctcagattat gagtgttgca tttaaattat gcctgggagt gccatcaaaa    240
acagactggg ttgctatcac tctctatgcc tgtgactcaa aaagtgaatt tcagaaatgg    300
gagtgcaaaa atgacacact tttggggatc aaaggagaag atttattttt taactacggc    360
aacagacaag aaaagaatat tatgctctac aagggatcgg gtttatggag caggtggaag    420
atctatggaa ccacagacaa tctgtgctcc agaggttatg aagccatgta tacgctacta    480
ggcaatgcca atggagcaac ctgtgcattc ccgttcaagt ttgaaaacaa gtggtacgca    540
gattgcacga gtgctgggcg gtcggatgga tggctctggt gcggaaccac tactgactat    600
gacacagaca agctatttgg atattgtcca ttgaaatttg agggcagtga aagcttatgg    660
aataaagacc cgctgaccag cgtttcctac cagataaact ccaaatccgc tttaacgtgg    720
caccaagcga ggaaaagctg ccaacaacag aacgctgagc tcctgagcat cacagagata    780
catgagcaaa catacctgac aggattaacc agttccttga cctcaggact ctggattgga    840
cttaacagtc tgagcttcaa cagcggttgg cagtggagtg accgcagtcc tttccgatat    900
ttgaactggt taccaggaag tccatcagct gaacctggaa aaagctgtgt gtcactaaat    960
cctgaaaaaa atgctaaatg ggaaaatctg gaatgtgttc agaaactggg ctatatttgc   1020
aaaaagggca acaccacttt aaattctttt gttattccct cagaaagtga tgtgcctact   1080
cactgtccta gtcagtggtg gccgtatgcc ggtcactgtt acaagattca cagagatgag   1140
aaaaaaatcc agagggatgc tctgaccacc tgcaggaagg aaggcggtga cctcacaagt   1200
atccacacca tcgaggaatt ggactttatt atctcccagc taggatatga gccaaatgac   1260
gaattgtgga tcggcttaaa tgacattaag attcaaatgt actttgagtg gagtgatggg   1320
accccctgtaa cgtttaccaa atggcttcgt ggagaaccaa gccatgaaaa caacagacag   1380
gaggattgtg tggtgatgaa aggcaaggat gggtactggg cagatcgggg ctgtgagtgg   1440
cctcttggct acatctgcaa gatgaaatca cgaagccaag gtccagaaat agtggaagtc   1500
gaaaaaggct gcaggaaagg ctggaaaaaa catcactttt actgctatat gattggacat   1560
acgctttcaa catttgcaga agcaaaccaa acctgtaata atgagaatgc ttatttaaca   1620
actattgaag acagatatga acaagccttc ctgactagtt tcgttggctt aaggcctgaa   1680
aaatatttct ggacaggact ttcagatata caaaccaaag gacttttca gtggaccatc   1740
gaggaagagg ttcggttcac ccactggaat tcagatatgc agggcgaaa gccagggtgt   1800
gttgccatga aaccgggat tgcaggggc ttatgggatg ttttgaaatg tgatgaaaag   1860
gcaaaatttg tgtgcaagca ctgggcagaa ggagtaaccc acccaccgaa gcccacgacg   1920
actcccgaac ccaaatgtcc ggaggattgg ggcgccagca gtagaacaag cttgtgtttc   1980
aagctgtatg caaaaggaaa acatgagaag aaaacgtggt ttgaatctcg agattttgt    2040
cgagctctgg gtggagactt agctagc                                       2067
```

MANNOSE RECEPTOR C TYPE 1 (MRC1) CODON OPTIMIZED CELL LINE AND USES THEREOF

CROSS REFERENCE TO RELATED APPLICATIONS

This application claims priority under 35 U.S.C. §371 to International Application No. PCT/US2011/044577, filed Jul. 19, 2011, which claims priority to U.S. Ser. No. 61/365,755, filed on Jul. 19, 2010. The contents of the aforementioned application are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 19, 2011, is named S20717WO.txt and is 30,622 bytes in size.

BACKGROUND

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. The deficiency in this enzyme causes glucocerebroside to accumulate in large quantities in the lysosomes of phagocytic cells located in the liver, spleen and bone marrow of Gaucher patients. Accumulation of these molecules causes a range of clinical manifestations including splenomegaly, hepatomegaly, skeletal disorder, thrombocytopenia and anemia. (Beutler et al. Gaucher disease; In: The Metabolic and Molecular Bases of Inherited Disease (McGraw-Hill, Inc, New York, 1995) pp. 2625-2639)

Treatments for patients suffering from this disease include administration of analgesics for relief of bone pain, blood and platelet transfusions and, in some cases, splenectomy. Joint replacement is sometimes necessary for patients who experience bone erosion. Enzyme replacement therapy with GCB has been used as a treatment for Gaucher disease.

SUMMARY

Some patients receiving enzyme replacement therapy with GCB can develop an immune response (e.g., neutralizing antibody) against the GCB treatment. For example, patients receiving enzyme replacement therapy with imiglucerase have developed an immune response. Methods of determining if a patient has developed an immune response to an enzyme replacement therapy are needed. The present invention is based, in part, on the discovery that the introduction of a nucleic acid sequence encoding mannose receptor, C type 1 (MRC1) into cells, e.g., eukaryotic or prokaryotic cells, can result in toxicity to the cell and ultimately result in an inversion of part of the sequence. It was discovered that codon optimization of at least a portion of the nucleic acid sequence encoding MRC1 allows for normal plasmid amplification, e.g., in prokaryotic cells and stable expression of MRC1 on the surface of cells, e.g., eukaryotic cells. The cells can be used, inter alia, to determine if a subject has developed antibodies (e.g., neutralizing antibodies) against a GCB treatment.

Therefore, invention relates, inter alia, to isolated nucleic acid molecules comprising nucleotide sequence encoding mannose receptor, C type 1 (MRC1) that include a 5' region of the nucleotide sequence that is codon optimized; cells comprising such nucleic acid molecules; and methods of detecting antibody production, e.g., neutralizing antibody production, in a subject being treated for Gaucher disease using such cells. The invention also relates, inter alia, to methods for selecting a treatment for a subject with Gaucher disease and selecting subjects for treatment with velaglucerase (e.g., alone or in combination with another therapy) using the cells described herein.

In some aspects, the disclosure features an isolated nucleic acid molecule comprising a nucleic acid sequence encoding MRC1, or a functional fragment thereof, that has a 5' region and a 3' region, wherein at least one codon of the 5' region is an optimized codon. For example, a sufficient number of codons in the 5' region are optimized codons such that when the isolated nucleic acid is introduced into a host cell and grown in culture at least about 10%, 20%, 30%, 40%, 50%, 60%, 70%, 80%, 90% or more of the cells do not have a rearrangement of at least part of the 5' region of the sequence encoding MRC1.

In some embodiments, the nucleic acid molecule has at least about 300, 350, 400, 450, 460, 470, 480, 490, 500, 510, 520, 530, 540, 550, or 600 residues in the 5' region that differ from the residues present in the 5' region of SEQ ID NO:1. In some embodiments, the nucleic acid molecule includes at least about 350, 360, 370, 380, 390, 400, 410, 420, 430, 440, 450, 500, 550, 600, 650, 680, or 689 codons that are optimized codons.

In some embodiments, the 5' region of the nucleic acid molecule differs from the 5' region of the nucleic acid of SEQ ID NO:1 by at least about 15%, 20%, 21%, 22%, 23%, 24%, 25%, 26%, 27%, 28%, 29% or 30% of the nucleic acid residues. In some embodiments, at least about 20%, 30%, 40%, 50%, 60%, 70%, 80%, 90%, 95%, 99% or all of the codons in the 5' region are optimized codons. In one embodiment, at least about 50%, 55%, 60%, 65%, 70%, 75%, 80%, 85%, 90%, 95%, 99% or all of the codons in the 5' region are optimized codons.

In some embodiments, the 5' region of the nucleic acid sequence is at least about 85%, 90%, 95%, 96%, 97%, 98% or 99% identical to the nucleic acid sequence of SEQ ID NO:2 or SEQ ID NO:3. In some embodiments, the 5' region of the nucleic acid sequence comprises or consists of the nucleic acid sequence of SEQ ID NO:2 or SEQ ID NO:3.

In some embodiments, the 3' region of the nucleic acid sequence comprises or consists of residues 2088 to 4371 of SEQ ID NO:1, or a functional fragment thereof. In some embodiments, the 3' region of the nucleic acid sequence is about 50%, 60%, 70%, 80%, 85%, 90%, 95%, 98%, or 99% identical to residues 2088 to 4371 of SEQ ID NO:1.

In some embodiments, the '3 region of the nucleic acid sequence includes at least one optimized codon. In one embodiment, at least about 10%, 20%, 30%, 40%, 50%, 60%, 70%, 80%, 90%, 95%, 99% or all of the codons of the 3' region are optimized codons.

In some embodiments, at least about 100, 200, 300, 400, 500, 500, 700, 750, 760, or 768 codons of the 3' region of the nucleic acid sequence are optimized codons.

In some embodiments, the nucleotide acid molecule encodes a mammalian MRC1 or a functional fragment thereof, e.g., a human MRC1 or a functional fragment thereof. In some embodiments, the nucleic acid molecule encodes an amino acid sequence that is at least about 90%, 95%, 96%, 97%, 98%, 99% or identical to the amino acid sequence of SEQ ID NO:4. In a preferred embodiment, the nucleic acid molecule encodes a polypeptide having the amino acid sequence of SEQ ID NO:4.

In some aspects, the disclosure features an expression vector comprising one or more of the nucleic acid molecules described herein. For example, the expression vector can be used for transient or stable expression of MRC1 or a functional portion thereof, in a cell, e.g., a prokaryotic cell (e.g., a bacterial cell) or a eukaryotic cell (e.g., a mammalian cell).

In some aspects, the disclosure features a cell (e.g., a recombinant cell) comprising one or more of the nucleic acid molecules described herein.

In some embodiments, the cell is a eukaryotic cell, e.g., a mammalian cell, e.g., a primary or secondary mammalian cell, e.g., a fibroblast, a blood cell, a myoblast, a keratinocyte, an epithelial cell, an endothelial cell, a glial cell, a neural cell, a muscle cell, and precursors of these cells. In a preferred embodiment, the cell is a human cell. In some embodiments, the cell is a primary or secondary fibrosarcoma cell line, e.g., a HT-1080 cell. In one embodiment, the cell is a yeast cell.

In some embodiments, the cell is a prokaryotic cell, e.g., a bacterial cell.

In some embodiments, the cell does not express an Fc receptor (e.g., human Fc receptor, e.g., human Fc-gamma receptor). For example, in some embodiments, the cell carries a mutation for, e.g., a knockout for, an Fc receptor (e.g., a human Fc receptor). The mutation can be one which reduces the expression of the gene, reduces protein or activity levels. The mutation can be one which reduces the level of the Fc receptor, e.g., one which reduces gene expression, e.g., a null mutation, e.g., a deletion, a frameshift or an insertion. In a preferred embodiment the mutation is a knockout, e.g., in the Fc receptor gene.

In some embodiments, the nucleic acid molecule described herein is introduced into the cell by transfection (e.g., stable transfection) or infection.

In one aspect, the disclosure features a method for detecting anti-GCB antibody (e.g., neutralizing antibody) in a sample (e.g., a patient sample, e.g., blood or serum) that reduces (e.g., inhibits) cellular uptake of GCB (e.g., velaglucerase or imiglucerase). The method includes:

providing a cell described herein that expresses MRC1, or a functional fragment thereof;

contacting the cell with a sample (e.g., a patient sample, e.g., blood or serum) and GCB;

detecting cellular uptake of the GCB into the cell, wherein the absence of cellular uptake or a decrease in cellular uptake as compared to a reference standard indicates that a subject has developed neutralizing antibodies to a GCB enzyme replacement therapy.

In one embodiment, the GCB is labeled, e.g., with a detectable label. The label can be a radioisotope, spin label, enzyme label, fluorescent group and chemiluminescent group. In one embodiment, the label is a fluorescent label and the fluorescent label is selected from, e.g., a green fluorescent dye, such as Alexa FLUOR® 488 or fluorescein isothiocyanate (FITC)).

In some embodiments, the method includes contacting the cell with the sample, contacting the cell with GCB, e.g., labeled GCB and removing unbound GCB and GCB bound to the cell surface (e.g., via trypsin digestion).

In some embodiments, the reference standard is the level of GCB (e.g., velaglucerase or imiglucerase) detected in the absence of the anti-GCB antibody (e.g., neutralizing antibody) under identical conditions.

In some embodiments, the cell does not express an Fc receptor (e.g., human Fc receptor, e.g., human Fc-gamma receptor). For example, in some embodiments, the cell carries a mutation for, e.g., a knockout for, an Fc receptor (e.g., a human Fc receptor). The mutation can be one which reduces the expression of the gene, reduces protein or activity levels. The mutation can be one which reduces the level of the Fc receptor, e.g., one which reduces gene expression, e.g., a null mutation, e.g., a deletion, a frameshift or an insertion. In a preferred embodiment, the mutation is a knockout, e.g., in the Fc receptor gene.

In some embodiments, the sample is from a subject that has been administered velaglucerase. In some embodiments, the sample is from a subject that has been administered imiglucerase.

In some aspects, the disclosure features a method of determining whether an anti-GCB (e.g., velaglucerase or imiglucerase) antibody (e.g., in a sample) reduces (e.g., inhibits) GCB (e.g., velaglucerase or imiglucerase) uptake in a cell. The method includes:

providing a cell described herein that expresses MRC1, or a functional fragment thereof;

contacting the cell with GCB and a sample (e.g., a patient sample, e.g., blood or serum) that comprises an anti-GCB antibody;

detecting cellular uptake of the GCB into the cell, wherein the absence of cellular uptake or a decrease in cellular uptake as compared to a reference standard indicates that the antibody reduces cellular uptake of GCB into the cell.

In one embodiment, the GCB is labeled, e.g., with a detectable label. The label can be a radioisotope, spin label, antigen label, enzyme label, fluorescent group and chemiluminescent group. In one embodiment, the label is a fluorescent label and the fluorescent label is selected from, e.g., a green fluorescent dye, such as Alexa FLUOR® 488 or fluorescein isothiocyanate (FITC)).

In some embodiments, the method includes contacting the cell with the sample, contacting the cell with GCB, e.g., labeled GCB, and removing unbound GCB and GCB bound to the cell surface (e.g., via trypsin digestion).

In some embodiments, the reference standard is the level of GCB (e.g., velaglucerase or imiglucerase) detected in the absence of the anti-GCB antibody (e.g., neutralizing antibody) under identical conditions.

In some embodiments, the cell does not express an Fc receptor (e.g., human Fc receptor, e.g., human Fc-gamma receptor). For example, in some embodiments, the cell carries a mutation for, e.g., a knockout for, an Fc receptor (e.g., a human Fc receptor). The mutation can be one which reduces the expression of the gene, reduces protein or activity levels. The mutation can be one which reduces the level of the Fc receptor, e.g., one which reduces gene expression, e.g., a null mutation, e.g., a deletion, a frameshift or an insertion. In a preferred embodiment, the mutation is a knockout, e.g., in the Fc receptor gene.

In some embodiments, the sample is from a subject that has been administered velaglucerase. In some embodiments, the sample is from a subject that has been administered imiglucerase.

In some aspects, the disclosure features a method of measuring cellular uptake (e.g., internalization) of GCB (e.g., velaglucerase or imiglucerase) into a cell. The method includes:

contacting a cell described herein that expresses MRC1, or a functional fragment thereof, with GCB; and measuring the amount of GCB (e.g., velaglucerase or imiglucerase) in the cell.

In some embodiments, the amount of GCB is measured about 1, about 2, about 3, about 4, about 5, about 6, or about 7 hours or overnight after the cell has been contacted with the GCB.

In some embodiments, the GCB is labeled, e.g., with a detectable label. The label can be a radioisotope, spin label, antigen label, enzyme label, fluorescent group and chemiluminescent group. In one embodiment, the label is a fluorescent label and the fluorescent label is selected from, e.g., a green fluorescent dye, such as Alexa FLUOR® 488 or fluorescein isothiocyanate (FITC)).

In some embodiments, the amount of uptake is measured by measuring GCB enzymatic activity in the cell. In some embodiments, a synthetic substrate such as a synthetic substrate that fluoresces upon cleavage (e.g., 4-MU-glc) is used to measure GCB enzymatic activity.

In some embodiments, the amount of uptake is measured by measuring intracellular GCB protein levels. In some embodiments, Western blot analysis is used. In some embodiments, immunohistochemistry analysis is used (e.g., immunohistochemistry on permeabilized cells).

In some embodiments, the cell is washed one or more times prior to the measuring step.

In some embodiments, the pH of the mixture (e.g., cell-GCB mixture) is about 7.5.

In some embodiments, the cell is contacted with GCB in the presence of one or more of: mannose-6-phosphate (M6P), mannan, and calcium.

In some embodiments, the amount of uptake is compared to a reference standard, e.g., the measured amount of uptake in the presence and absence of mannose-6-phosphate, the measured amount of uptake in the presence and absence of mannan, or the measured amount of uptake in the presence and absence of calcium.

In some embodiments, the GCB is velaglucerase. In some embodiments, the GCB is imiglucerase.

In some embodiments, the amount of uptake of velaglucerase is compared to the amount of uptake of imiglucerase (e.g., under the same conditions).

In another aspect, the disclosure features a method for identifying a subject as suitable for (e.g., being a candidate for) treatment with GCB enzyme replacement therapy (e.g., velaglucerase). The method includes evaluating the subject (e.g., measuring) for the presence of antibodies (e.g., neutralizing antibodies) to a GCB enzyme replacement therapy (e.g., the therapy currently being administered to the subject, e.g., imiglucerase) using a method described herein; and identifying the subject as suitable for treatment with an alternative Gaucher disease treatment (e.g., treatment with velaglucerase), e.g., if the determined value is greater than the value for the standard, e.g., by more than about 5%, about 10%, about 15%, about 20%, about 25%, about 30%, about 35%, about 40%, about 45%, about 50%, about 55%, about 60%, about 65%, about 70%, about 75%, about 80%, about 85%, or about 90%.

The evaluating can be performed, e.g., about every week, about every two weeks, about every three weeks, about every four weeks, about every two months, about every three months, about every four months, about every five months, about every six months, about every seven months, about every eight months, about every nine months, about every ten months, about every eleven months, or about every twelve months during the course of treatment. The evaluating can also be performed prior to commencing treatment (e.g., to establish a baseline value).

Based on the determination, a treatment decision can be made for the subject. For example, if a subject receiving a treatment for Gaucher disease, such as a GCB enzyme replacement therapy, e.g., imiglucerase, has a value for antibody that differs from the value for the standard, a decision can be made to transfer the subject currently receiving the GCB enzyme replacement treatment (e.g., imiglucerase treatment) to a different GCB enzyme replacement treatment (e.g., velaglucerase treatment). For example, if antibodies (e.g., neutralizing antibodies) to imiglucerase are detected in a subject undergoing treatment with imiglucerase, the subject can be transferred to treatment with velaglucerase.

Optionally, the method can include providing the treatment to the subject, e.g., wherein providing includes administering the treatment or transferring the treatment to the subject's possession.

In another aspect, the disclosure provides a method of selecting a treatment for administration to a subject with Gaucher disease. The method includes evaluating (e.g., measuring) the subject for the presence of antibodies (e.g., neutralizing antibodies) to a GCB enzyme replacement therapy (e.g., the therapy currently being administered to the subject, e.g., imiglucerase) using a method described herein.

Optionally, the method can include providing the treatment to the subject, e.g., wherein providing includes administering the treatment or transferring the treatment to the subject's possession.

In another aspect, the disclosure provides a method of selecting a treatment for administration to a subject who needs to increase cellular GCB uptake. The method includes evaluating (e.g., measuring) the subject for the presence of antibodies (e.g., neutralizing antibodies) to a GCB enzyme replacement therapy (e.g., the therapy currently being administered to the subject, e.g., imiglucerase) using a method described herein.

Optionally, the method can include providing the treatment to the subject, e.g., wherein providing includes administering the treatment or transferring the treatment to the subject's possession.

In some aspects, the disclosure features a method of treating a subject with Gaucher disease (e.g., type I Gaucher disease). The method includes:

selecting a subject with Gaucher disease that has received a GCB enzyme replacement therapy (e.g., imiglucerase) and has the presence of antibodies (e.g., neutralizing antibodies) to the GCB enzyme replacement therapy (e.g., imiglucerase) as determined by a method described herein; and administering velaglucerase to the subject.

In some embodiments, velaglucerase is administered at a dose of about 15 to about 60 U/kg (e.g. about 30 U/kg to about 60 U/kg, e.g., about 15 U/kg, 30 U/kg, 45 U/kg, or 60 U/kg), at a dose equal to or below about 22.5 U/kg, at a dose between about 22.5 and about 37.5 U/kg, at a dose between about 37.5 and about 52.5 U/kg, or at a dose equal to or above about 52.5 U/kg. In some embodiments, velaglucerase is administered at a dose of about 2.5 U/kg to about 60 U/kg. In some embodiments, the velaglucerase is administered every other week by intravenous infusion. In other embodiments, the velaglucerase is administered every week by intravenous infusion. In some embodiments, the velaglucerase is administered three times a week by intravenous infusion, e.g., at a dose of about 2.5 U/kg.

In some embodiments, the infusion of the dose (e.g., a dose of about 15 to about 60 U/kg, a dose of about 30 to about 60 U/kg, a dose equal to or below about 22.5 U/kg, a dose between about 22.5 and about 37.5 U/kg, a dose between about 37.5 and about 52.5 U/kg, a dose equal to or above about 52.5 U/kg, or a dose of about 15 U/kg, 30 U/kg, 45 U/kg, or 60 U/kg) occurs over about 60 minutes.

In another aspect, the disclosure provides a method of prescribing a GCB enzyme replacement therapy (e.g., imiglucerase or velaglucerase). The method includes:

receiving an identifier for the GCB enzyme replacement therapy, e.g., the chemical structure, chemical name, trade name or generic name of the GCB enzyme replacement therapy;

receiving information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) to the treatment, e.g., as determined by a method described herein.

selecting a subject in need of the GCB enzyme replacement therapy, e.g., on the basis that the subject needs to decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake; and causing the GCB enzyme replacement therapy to be prescribed, dispensed, or administered to a subject.

In another aspect, the disclosure provides a method of providing a recipient with information about, or with guidelines for, the use of a GCB enzyme replacement therapy (e.g., imiglucerase or velaglucerase). The method includes:

communicating to the recipient an identifier for the GCB enzyme replacement therapy, e.g., the chemical structure, chemical name, trade name or generic name of the GCB enzyme replacement therapy;

communicating to the recipient information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein;

receiving a request from the recipient to purchase the GCB enzyme replacement therapy; and selling, shipping or transferring the GCB enzyme replacement therapy to the recipient.

In another aspect, the disclosure features a method of providing a recipient with information about a GCB enzyme replacement therapy (e.g., imiglucerase or velaglucerase), or with guidelines for, the use of a GCB enzyme replacement therapy (e.g., imiglucerase or velaglucerase). The method includes:

providing an identifier for the GCB enzyme replacement therapy, e.g., the chemical structure, chemical name, trade name or generic name of the GCB enzyme replacement therapy;

providing information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein;

memorializing the identifier and the information; and transferring the memorialization (e.g., the memorialized identifier and information) to the recipient.

In another aspect, the disclosure provides a method of providing a recipient with information about a GCB enzyme replacement therapy (e.g., imiglucerase or velaglucerase), or with guidelines for the use of a GCB enzyme replacement therapy (e.g., imiglucerase or velaglucerase). The method includes:

providing an identifier for the GCB enzyme replacement therapy, e.g., the chemical structure, chemical name, trade name or generic name of the GCB enzyme replacement therapy;

providing information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein;

associating the identifier with the information, e.g., in a database or by physical association; and transferring the associated identifier and information to the recipient.

In another aspect, the disclosure provides a database, medium, or computer containing or programmed to contain:

an identifier for a GCB enzyme replacement therapy (e.g., imiglucerase or velaglucerase), e.g., the chemical structure, chemical name, trade name or generic name of the GCB enzyme replacement therapy;

information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein; and an associative function associating the identifier with the information, e.g., in a database or by physical association.

In another aspect, the disclosure provides a method of making a GCB enzyme replacement therapy (e.g., imiglucerase or velaglucerase) available to a subject. The method includes:

providing to the subject an identifier for the GCB enzyme replacement therapy, e.g., the chemical structure, chemical name, trade name or generic name of the GCB enzyme replacement therapy;

providing to the subject information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein; and placing into commerce, a dose of the GCB enzyme replacement therapy which can be administered to, provided to, or purchased by the subject.

In another aspect, the disclosure provides a method of causing a subject to request a GCB enzyme replacement therapy (e.g., imiglucerase or velaglucerase). The method includes:

providing to the subject an identifier for the GCB enzyme replacement therapy, e.g., the chemical structure, chemical name, trade name or generic name of the GCB enzyme replacement therapy;

providing to the subject information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein; and placing into commerce, a dose of the GCB enzyme replacement therapy which can be administered to, provided to, or purchased by the subject.

In another aspect, the disclosure provides a method for a subject to determine if a GCB enzyme replacement therapy (e.g., imiglucerase or velaglucerase) is appropriate for the subject. The method includes:

receiving an identifier for a GCB enzyme replacement therapy, e.g., the chemical structure, chemical name, trade name or generic name of the GCB enzyme replacement therapy;

receiving information that the GCB enzyme replacement therapy can decrease the likelihood (e.g., relative to a standard, e.g., a standard described herein, e.g., the likelihood for a cohort of subjects receiving a different treatment (e.g., imiglucerase) for Gaucher disease) of production of antibodies (e.g., neutralizing antibodies) that reduces (e.g., inhibits) cellular GCB uptake as determined by a method described herein; and contacting a healthcare provider to request treatment with or information about the GCB enzyme replacement therapy.

In another aspect, the disclosure features a method of selecting a payment class for a course of treatment with a GCB enzyme replacement therapy (e.g., imiglucerase or velaglucerase) for a subject with Gaucher disease (e.g., type I Gaucher disease). The method includes:

providing (e.g., receiving) an evaluation of whether or not the subject produces antibodies (e.g., neutralizing antibodies) that reduces (e.g., inhibits) cellular GCB uptake, using a method described herein; and performing at least one of (1) if the subject produces antibodies (e.g., neutralizing antibodies) to the GCB enzyme replacement therapy selecting a first payment class, and (2) if the subject does not produces antibodies (e.g., neutralizing antibodies) to the GCB enzyme replacement therapy selecting a second payment class.

In some embodiments, assignment of the subject is to the first class and the assignment authorizes payment for a course of treatment (e.g., velaglucerase).

In some embodiments, assignment of the subject is to the second class and the assignment authorizes payment for a course of treatment (e.g., imiglucerase or velaglucerase).

In one aspect, the disclosure features a method of providing information on which to make a decision about a subject with Gaucher disease (e.g., type I Gaucher disease), or making such a decision. The method includes providing (e.g., by receiving) an evaluation of a subject, wherein the evaluation was made by a method described herein, e.g., by optionally, administering a GCB enzyme replacement therapy (e.g., imiglucerase or velaglucerase), to the subject; providing a determination post administration of whether or not the subject produces antibodies (e.g., neutralizing antibodies) that reduces (e.g., inhibits) cellular GCB uptake using a method described herein, thereby providing a post administration determination; providing a comparison of the post administration determination with a standard (e.g., a standard described herein), thereby, providing information on which to make a decision about a subject, or making such a decision.

In some embodiments, the method includes making the decision.

In some embodiments, the method also includes communicating the information to another party (e.g., by computer, compact disc, telephone, facsimile, email, or letter).

In some embodiments, the decision includes selecting a subject for payment, making or authorizing payment for a first course of action (e.g., treatment with velaglucerase) if the subject produces antibodies (e.g., neutralizing antibodies) to the GCB enzyme replacement therapy and a second course of action (e.g., treatment with imiglucerase or velaglucerase) if the subject does not produces antibodies (e.g., neutralizing antibodies) to the GCB enzyme replacement therapy.

In some embodiments, the subject produces antibodies (e.g., neutralizing antibodies) to the GCB enzyme replacement therapy and the course of action is authorization of a course of therapy (e.g., treatment with velaglucerase).

In some embodiments, the subject produces antibodies (e.g., neutralizing antibodies) to the GCB enzyme replacement therapy and the course of action is assigning the subject to a first class. In some embodiments, assignment to the first class will enable payment for a treatment (e.g., velaglucerase) provided to the subject. In some embodiments, payment is by a first party to a second party. In some embodiments, the first party is other than the subject. In some embodiments, the first party is selected from a third party payer, an insurance company, an employer, an employer sponsored health plan, an HMO, or a governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In some embodiments, the subject does not produce antibodies (e.g., neutralizing antibodies) to the GCB enzyme replacement therapy and the course of action is authorization of a course of therapy (e.g., imiglucerase or velaglucerase).

In some embodiments, the subject does not produce antibodies (e.g., neutralizing antibodies) to the GCB enzyme replacement therapy and the course of action is assigning the subject to a second class. In some embodiments, assignment to the second class will enable payment for a treatment (e.g., imiglucerase or velaglucerase) provided to the subject. In some embodiments, payment is by a first party to a second party. In some embodiments, the first party is other than the subject. In some embodiments, the first party is selected from a third party payer, an insurance company, an employer, an employer sponsored health plan, an HMO, or a governmental entity. In some embodiments, the second party is selected from the subject, a healthcare provider, a treating physician, an HMO, a hospital, a governmental entity, or an entity which sells or supplies the treatment. In some embodiments, the first party is an insurance company and the second party is selected from the subject, a healthcare provider, a treating physician, an HMO, a hospital, a governmental entity, or an entity which sells or supplies the treatment. In some embodiments, the first party is a governmental entity and the second party is selected from the subject, a healthcare provider, a treating physician, an HMO, a hospital, an insurance company, or an entity which sells or supplies the treatment.

In another aspect, the disclosure features a method of selecting a payment class for a course of treatment with a GCB enzyme replacement therapy (e.g., velaglucerase) for a subject with Gaucher disease (type I Gaucher disease). The method includes determining that antibodies (e.g., neutralizing antibodies) to the GCB enzyme replacement therapy are present in the subject using a method described herein, and approving, making, authorizing, receiving, transmitting or otherwise allowing payment of a selected course of treatment, e.g., velaglucerase.

In another aspect, the disclosure features a method of selecting a payment class for a course of treatment with a GCB enzyme replacement therapy (e.g., imiglucerase or velaglucerase) for a subject with Gaucher disease (type I Gaucher disease). The method includes determining that antibodies (e.g., neutralizing antibodies) to the GCB enzyme replacement therapy are not present in the subject using a method described herein, and approving, making, authorizing, receiving, transmitting or otherwise allowing payment of a selected course of treatment, e.g., imiglucerase or velaglucerase.

In one aspect, the disclosure features a method of making a data record. The method includes entering the result of a method described herein into a record, e.g., a computer readable record. In some embodiments, the record is available on the World Wide Web. In some embodiments, the record is evaluated by and/or transmitted to a third party payer, an insurance company, an employer, an employer sponsored health plan, an HMO, a governmental entity, a healthcare provider, a treating physician, a hospital, or an entity which sells or supplies the treatment, or is otherwise relied on in a method described herein.

In another aspect, the disclosure features a data record (e.g., computer readable record), wherein the record includes results from a method described herein. In some embodiments, the record is available on the World Wide Web. In some embodiments, the record is evaluated by and/or transmitted to a third party payer, an insurance company, an employer, an employer sponsored health plan, an HMO, a governmental entity, a healthcare provider, a treating physician, a hospital, or an entity which sells or supplies the treatment.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, an HMO, a hospital, a governmental entity, or an entity which sells or supplies the treatment. In some embodiments, the second party is a third party payer, an insurance company, an employer, an employer sponsored health plan, an HMO, or a governmental entity. In some embodiments, the first party is selected from the subject, a healthcare provider, a treating physician, an HMO, a hospital, an insurance company, or an entity which sells or supplies the treatment and the second party is a governmental entity. In some embodiments, the first party is selected from the subject, a healthcare provider, a treating physician, an HMO, a hospital, an insurance company, or an entity which sells or supplies the treatment and the second party is an insurance company.

In one aspect, the disclosure features a method of transmitting a record described herein. The method includes a first party transmitting the record to a second party, e.g., by computer, compact disc, telephone, facsimile, email, or letter. In some embodiments, the second party is selected from the subject, a healthcare provider, a treating physician, an HMO, a hospital, a governmental entity, or an entity which sells or supplies the treatment. In some embodiments, the first party is an insurance company or government entity and the second party is selected from the subject, a healthcare provider, a treating physician, an HMO, a hospital, a governmental entity, or an entity which sells or supplies the treatment. In some embodiments, the first party is a governmental entity or insurance company and the second party is selected from the subject, a healthcare provider, a treating physician, an HMO, a hospital, an insurance company, or an entity which sells or supplies the treatment.

In one method, information about whether or not a subject with Gaucher disease produces antibodies (e.g., neutralizing antibodies) to the GCB enzyme replacement therapy as determined by a method described herein (e.g., wherein the information is obtained as described herein) is provided (e.g., communicated, e.g., electronically communicated) to a third party, e.g., a hospital, clinic, a government entity, a reimbursing party or insurance company (e.g., a life insurance company). For example, choice of medical procedure, payment for a medical procedure, payment by a reimbursing party, or cost for a service or insurance can be function of the information. For example, the third party receives the information, makes a determination based at least in part on the information, and optionally communicates the information or makes a choice of procedure, payment, level of payment, coverage, etc. based on the information.

In one embodiment, a premium for insurance (e.g., life or medical) is evaluated as a function of information about whether or not a subject with Gaucher disease produces antibodies (e.g., neutralizing antibodies) to the GCB enzyme replacement therapy, as determined by a method described herein. For example, premiums can be increased (e.g., by a certain percentage) if the subject produces antibodies (e.g., neutralizing antibodies) to the GCB enzyme replacement therapy, as determined by a method described herein.

Information about whether or not a subject with Gaucher disease produces antibodies (e.g., neutralizing antibodies) to the GCB enzyme replacement therapy as determined by a method described herein can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on whether or not a subject with Gaucher disease produces antibodies (e.g., neutralizing antibodies) to the GCB enzyme replacement therapy. An insurance premium or risk assessment can also be evaluated as function of whether or not a subject with Gaucher disease produces antibodies (e.g., neutralizing antibodies) to the GCB enzyme replacement therapy.

In one embodiment, information about whether or not a subject with Gaucher disease produces antibodies (e.g., neutralizing antibodies) to the GCB enzyme replacement therapy is analyzed by a function that determines whether to authorize the transfer of funds to pay for a service or treatment provided to a subject (or make another decision referred to herein). For example, the results (e.g., that the subject produces antibodies (e.g., neutralizing antibodies) to the GCB enzyme replacement therapy) may indicate that a subject is suitable for treatment (e.g., velaglucerase), suggesting that a treatment course (e.g., with velaglucerase) is needed, thereby triggering an outcome that indicates or causes authorization to pay for a service or treatment (e.g., velaglucerase) provided to a subject. For example, an entity, e.g., a hospital, a care giver, a government entity, or an insurance company or other entity which pays for, or reimburses medical expenses, can use the outcome of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, a physician, or other care-giver, for a service or treatment (e.g., velaglucerase) provided to a patient. For example, a first entity, e.g., an insurance company, can use the outcome of a method described herein to determine whether to continue, discontinue, enroll an individual in an insurance plan or program, e.g., a health insurance or life insurance plan or program.

In some aspects, the disclosure features a kit comprising a cell or a plurality of cells described herein. In some embodiments, the kit further includes instructions on one or more of how to use the cell or plurality of cells. For example, the instructions can include information regarding how to determine cellular uptake of GCB and/or how to detect the presence of an antibody to a GCB enzyme replacement therapy. In some embodiments, the kit can further comprise one or more additional agents. For example the kit can include one or more of: labeled GCB, e.g., a labeled GCB described herein; a substrate which indicates enzymatic activity of GCB within a cell (e.g., a synthetic substrate that fluoresces upon cleavage, e.g., 4-MU-glc); an agent (e.g., an antibody) for measuring intracellular GCB protein levels; mannan; mannose-6-phosphate; and calcium.

The term "isolated" refers to a molecule that is substantially free of its natural environment.

A "functional fragment" of MRC1 refers to a fragment of MCR1 that is expressed on the surface of a cell such that it binds to and internalizes GCB.

The term "5' region" of a nucleic acid sequence encoding MRC1 refers to nucleic acid residues corresponding to the positions 1 to 2067 of the nucleic acid sequence of SEQ ID NO:1.

The term "3' region" of a nucleic acid sequence encoding MRC1 refers to nucleic acid residues corresponding to the positions 2068 to 4371 of the nucleic acid sequence of SEQ ID NO:1, or a functional fragment thereof.

The term "optimized codon" refers to the following codons: Ala (gcc); Arg (aga); Asn (aac); Asp (gac); Cys (ugc); Gln (cag); Gly (ggc); H is (cac); Ile (auc); Leu (cug); Lys (aag); Pro (ccc); Phe (uuc); Ser (agc); Thr (acc); Tyr (uac); Glu (gag); and Val (gug). All codons other than optimized codons are "non-common codons".

As used herein, the term "about" refers to up to ±10% of the value qualified by this term. For example, about 50 mM refers to 50 mM±5 mM; about 4% refers to 4%±0.4%.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" or "identity" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The term "subject" refers to any mammal, including but not limited to, any animal classified as such, including humans, non-human primates, primates, baboons, chimpanzees, monkeys, rodents (e.g., mice, rats), rabbits, cats, dogs, horses, cows, sheep, goats, pigs, etc. The term "subject" can be used interchangeably with the term "patient."

The terms "therapeutically effective dose," and "therapeutically effective amount," refer to that amount of a compound that results in prevention of symptoms (e.g., prevention of about 80%, about 85%, about 90%, about 95%, about 96%, about 97%, about 98%, or about 99% of symptoms, e.g., symptoms of Gaucher disease in a subject diagnosed as having Gaucher disease), delay of onset of symptoms, or amelioration of symptoms of Gaucher disease. A therapeutically effective amount will, for example, be sufficient to treat, prevent, reduce the severity, delay the onset, and/or reduce the risk of occurrence of one or more symptoms of a disorder associated with Gaucher disease. The effective amount can be determined by methods well known in the art and as described in subsequent sections of this description.

The terms "treatment" and "therapeutic method" refer to treatment of an existing disorder and/or prophylactic/preventative measures. Those in need of treatment may include individuals already having a particular medical disorder, as well as those at risk or having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder.

The term "treating" refers to administering a therapy in an amount, manner, and/or mode effective to improve or prevent a condition, symptom, or parameter associated with a disorder (e.g., a disorder described herein) or to prevent onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject.

All publications, patent applications, patents, and other references mentioned herein are incorporated by reference in their entirety. In the case of conflict, the present specification, including definitions, controls. In addition, the materials, methods, and examples are illustrative only and not intended to be limiting.

The details of one or more embodiments of the invention are set forth in the accompanying drawings and the description below.

BRIEF DESCRIPTION OF DRAWINGS

Figure 1C:
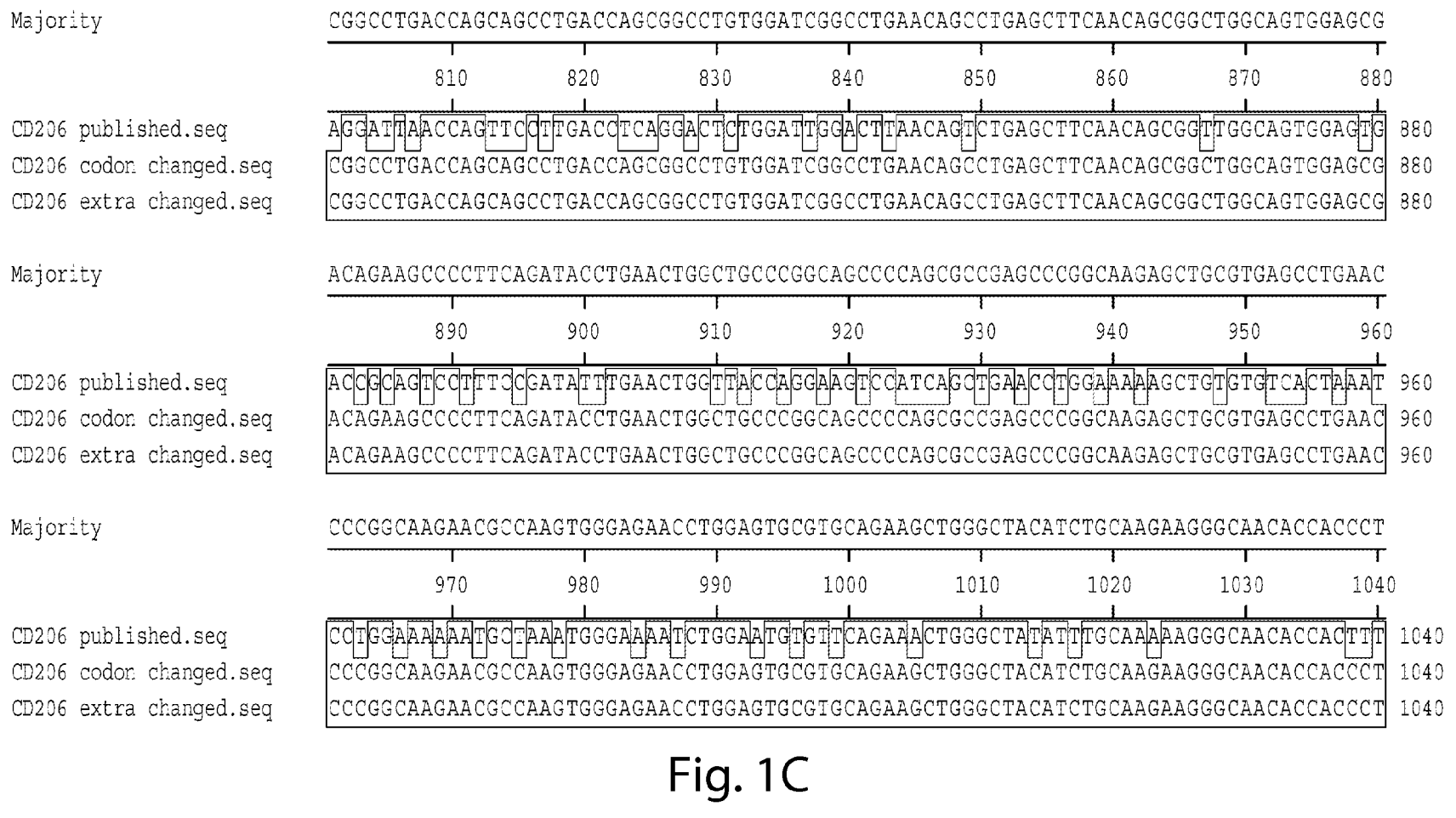
Figure 1C:
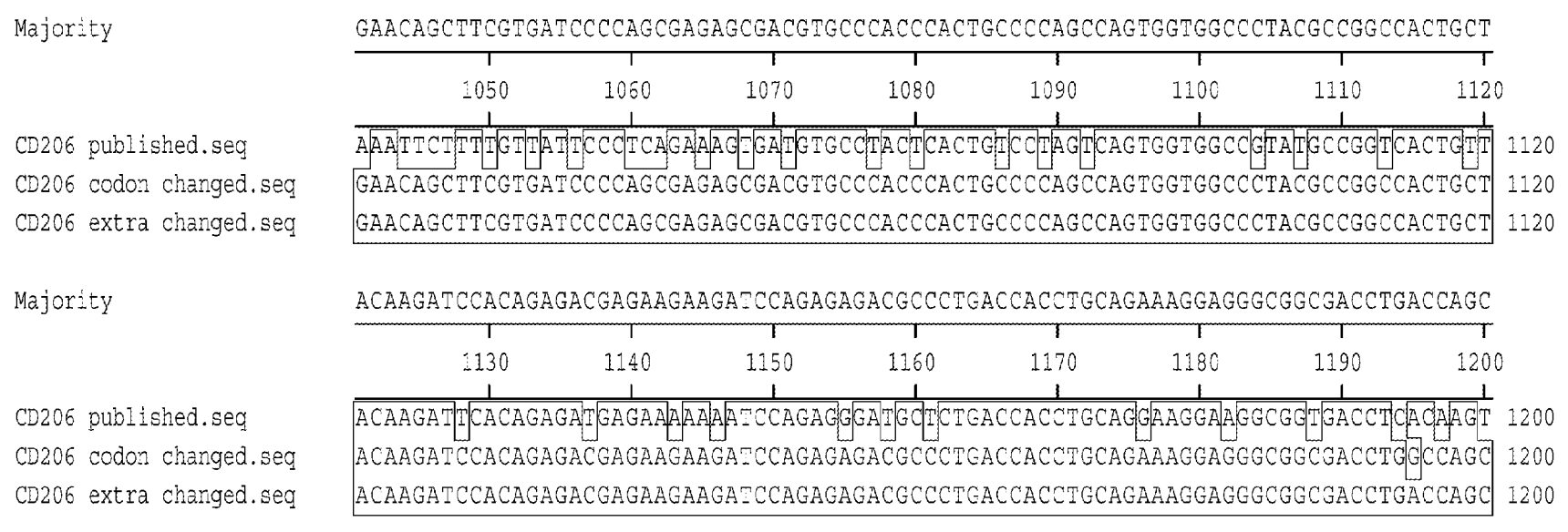

FIGS. 1A-1E depict a nucleotide sequence alignment of 5' region of wild-type (SEQ ID NO: 8) and codon optimized (SEQ ID NOS: 2-3, respectively, in order of appearance) human MRC1 gene sequences. FIGS. 1A-1E disclose the "Majority" sequence as SEQ ID NO: 7.

DETAILED DESCRIPTION

Figure 1A:
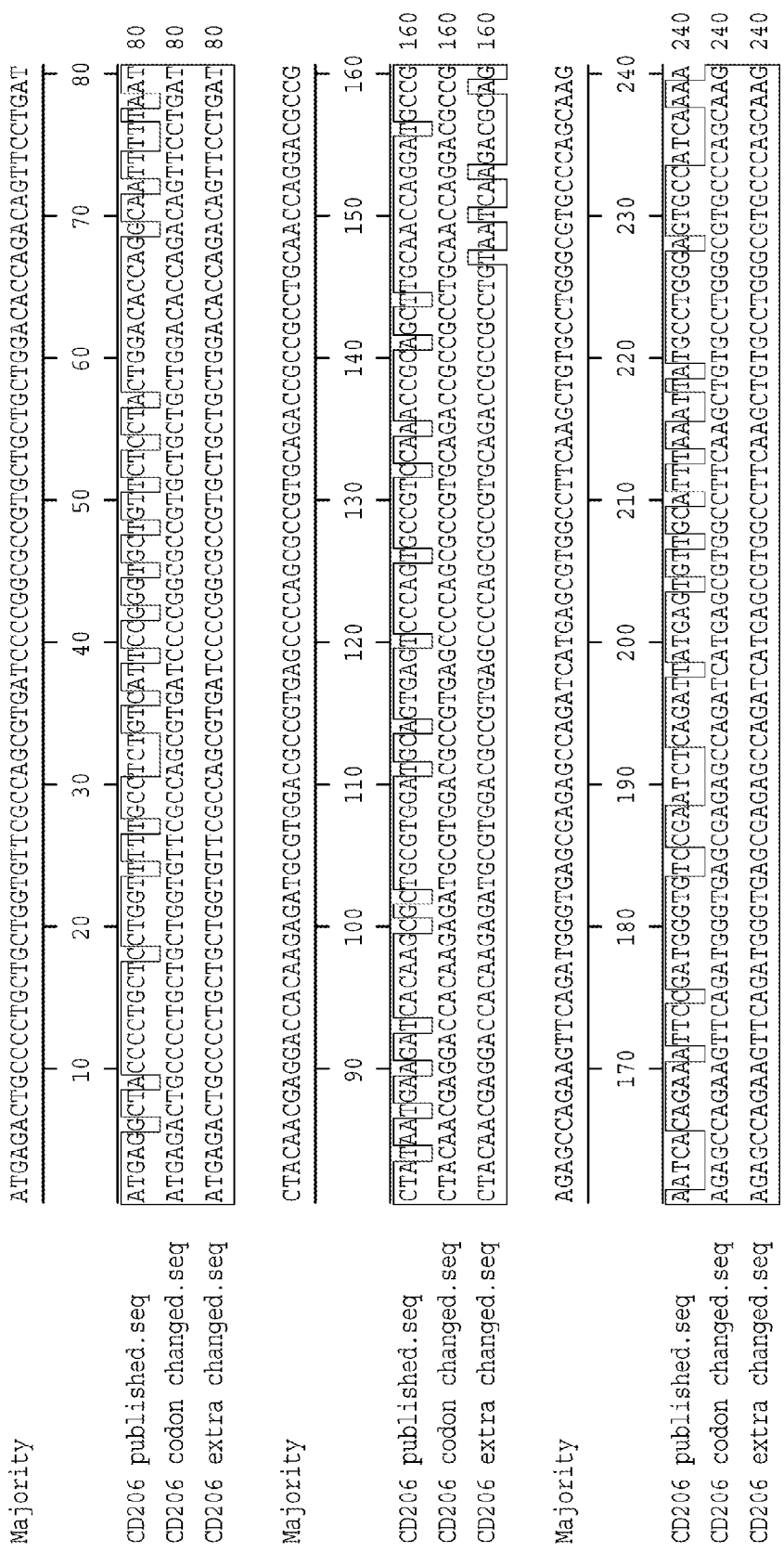
Figure 1A:
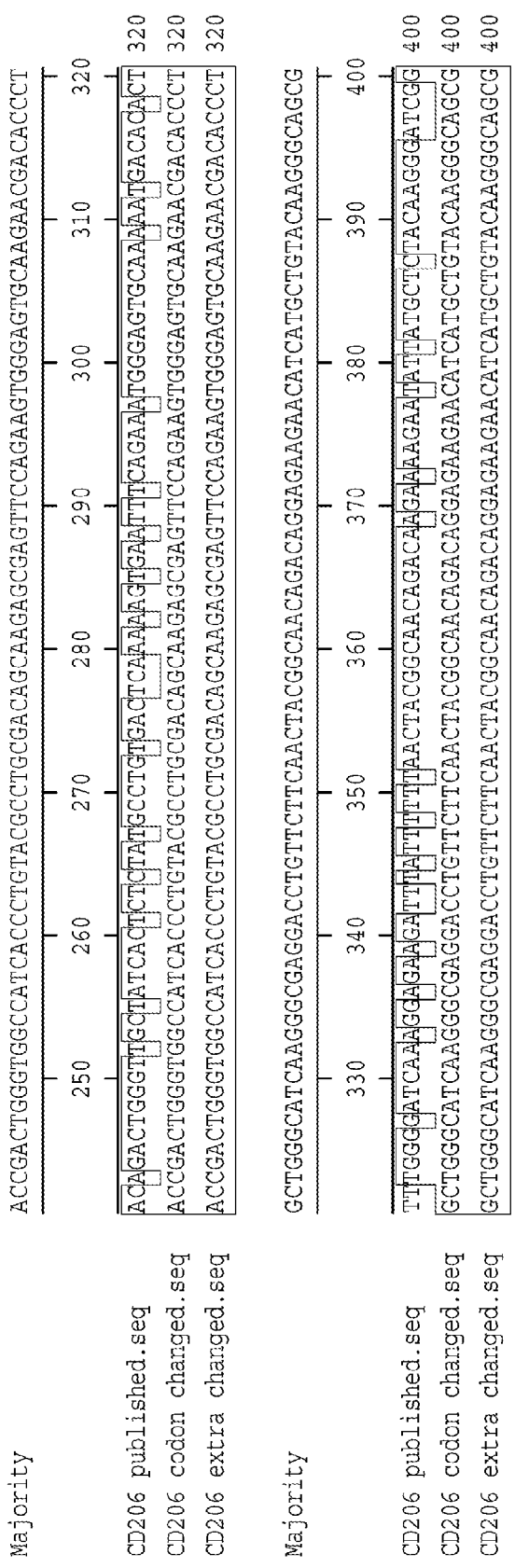
Figure 1B:
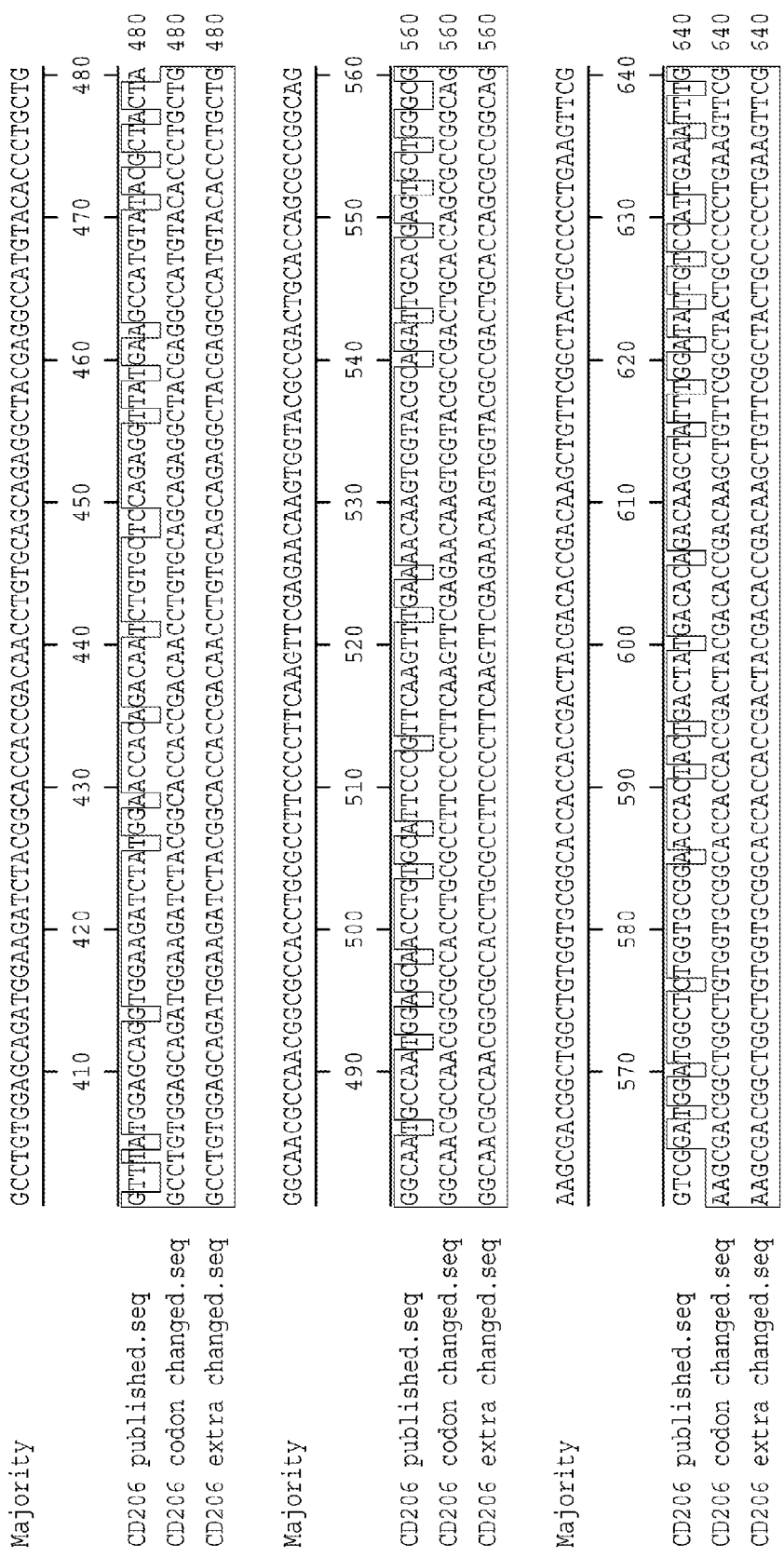
Figure 1D:
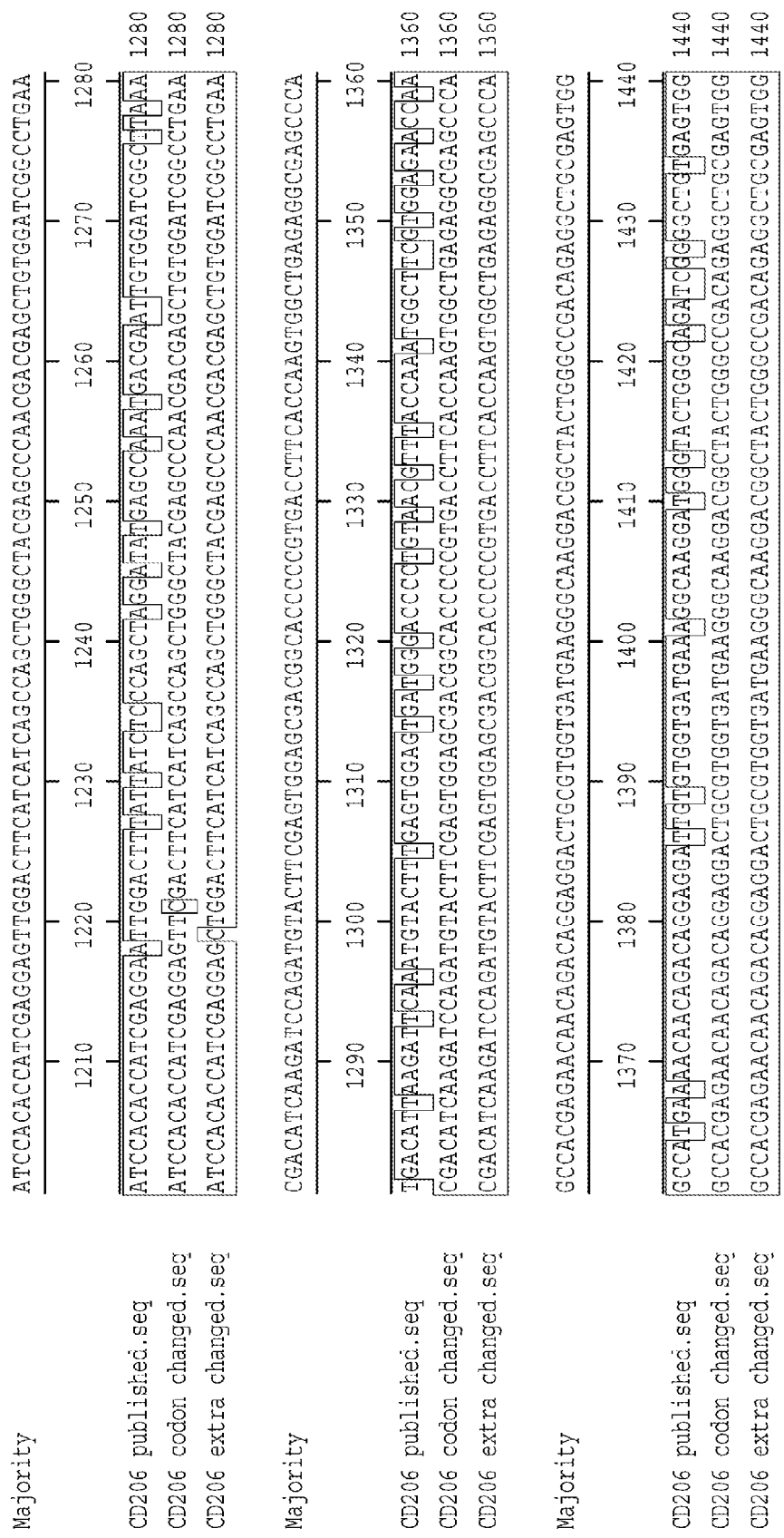
Figure 1E:
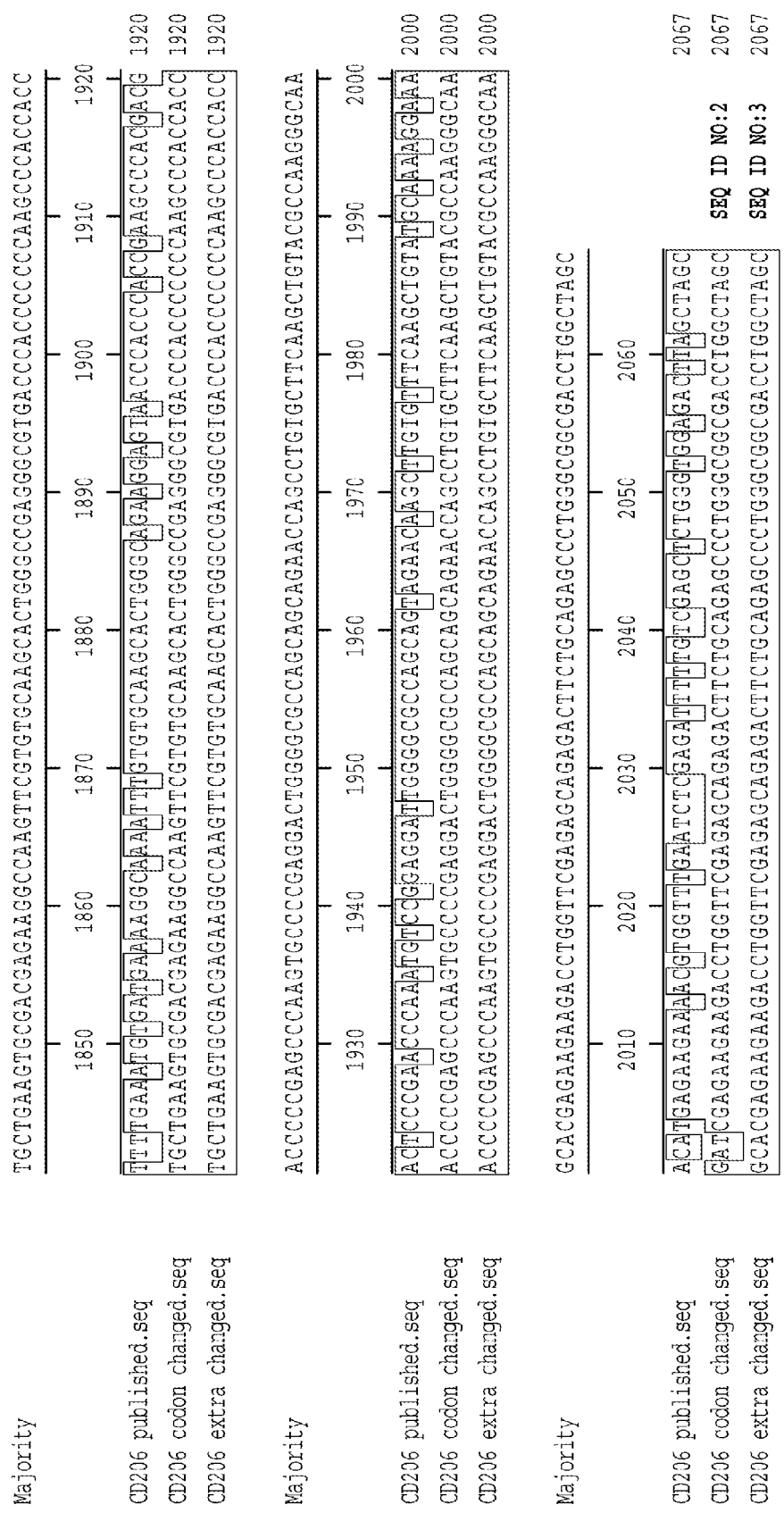

The invention relates, inter alia, to isolated nucleic acid molecules comprising nucleotide sequence encoding mannose receptor, C type 1 (MRC1) that include a 5' region of the nucleotide sequence that is codon optimized; cells comprising such nucleic acid molecules; and methods of detecting antibody production, e.g., neutralizing antibody production, in a subject being treated for Gaucher disease using such cells. The invention also relates, inter alia, to methods for selecting a treatment for a subject with Gaucher disease and selecting subjects for treatment with velaglucerase (e.g., alone or in combination with another therapy) using the cells described herein.

Mannose Receptor, C Type 1 (MRC1)

Mannose Receptor, C Type 1 (MRC1), also known CD206, MMR, RP11-457D2.1, CLEC13D, C-type lectin domain family 13 member D, macrophage mannose receptor 1, is a type I membrane receptor that mediates the endocytosis of glycoproteins by macrophages. The recognition of complex carbohydrate structures on glycoproteins plays a role in several biological processes, including cell-cell recognition, serum glycoprotein turnover, and neutralization of pathogens. This gene is in close proximity to MRC1L1. The gene loci including this gene, MRC1L1, as well as LOC340843 and LOC340893, consist of two nearly identical, tandemly linked genomic regions, which are thought to be a part of a duplicated region.

Human MRC1 coding region nucleotide sequence (SEQ ID NO:1, NCBI Accession: NM_002438)

```
   1 atgaggctac ccctgctcct ggttttttgcc tctgtcattc cgggtgctgt tctcctactg
  61 gacaccaggc aattttaat ctataatgaa gatcacaagc gctgcgtgga tgcagtgagt
 121 cccagtgccg tccaaaccgc agcttgcaac caggatgccg aatcacagaa attccgatgg
 181 gtgtccgaat ctcagattat gagtgttgca tttaaattat gcctgggagt gccatcaaaa
 241 acagactggg ttgctatcac tctctatgcc tgtgactcaa aaagtgaatt tcagaaatgg
 301 gagtgcaaaa atgacacact tttgggatc aaaggagaag atttatttt taactacggc
 361 aacagacaag aaaagaatat tatgctctac aagggatcgg gtttatggag caggtggaag
 421 atctatggaa ccacagacaa tctgtgctcc agaggttatg aagccatgta tacgctacta
 481 ggcaatgcca atggagcaac ctgtgcattc ccgttcaagt ttgaaaacaa gtggtacgca
 541 gattgcacga gtgctgggcg gtcggatgga tggctctggt gcggaaccac tactgactat
 601 gacacagaca agctatttgg atattgtcca ttgaaatttg agggcagtga aagcttatgg
 661 aataaagacc cgctgaccag cgttcctac cagataaact ccaaatccgc tttaacgtgg
 721 caccaagcga ggaaaagctg ccaacaacag aacgctgagc tcctgagcat cacagagata
 781 catgagcaaa catacctgac aggattaacc agttccttga cctcaggact ctggattgga
 841 cttaacagtc tgagcttcaa cagcggttgg cagtggagtg accgcagtcc tttccgatat
 901 ttgaactggt taccaggaag tccatcagct gaacctggaa aaagctgtgt gtcactaaat
 961 cctggaaaaa atgctaaatg ggaaaatctg aatgtgttc agaaactggg ctatatttgc
1021 aaaaagggca acaccacttt aaattctttt gttattccct cagaaagtga tgtgcctact
1081 cactgtccta gtcagtggtg gccgtatgcc ggtcactgtt acaagattca cagagatgag
1141 aaaaaaatcc agagggatgc tctgaccacc tgcaggaagg aaggcggtga cctcacaagt
1201 atccacacca tcgaggaatt ggactttatt atctcccagc taggatatga gccaaatgac
1261 gaattgtgga tcggcttaaa tgacattaag attcaaatgt actttgagtg gagtgatggg
```

-continued

```
1321 acccctgtaa cgtttaccaa atggcttcgt ggagaaccaa gccatgaaaa caacagacag
1381 gaggattgtg tggtgatgaa aggcaaggat gggtactggg cagatcgggg ctgtgagtgg
1441 cctcttggct acatctgcaa gatgaaatca cgaagccaag gtccagaaat agtggaagtc
1501 gaaaaaggct gcaggaaagg ctggaaaaaa catcactttt actgctatat gattggacat
1561 acgctttcaa catttgcaga agcaaaccaa acctgtaata atgagaatgc ttatttaaca
1621 actattgaag acagatatga acaagccttc ctgactagtt tcgttggctt aaggcctgaa
1681 aaatatttct ggacaggact ttcagatata caaaccaaag gacttttca gtggaccatc
1741 gaggaagagg ttcggttcac ccactggaat tcagatatgc cagggcgaaa gccagggtgt
1801 gttgccatga gaaccgggat tgcaggggggc ttatgggatg ttttgaaatg tgatgaaaag
1861 gcaaaatttg tgtgcaagca ctgggcagaa ggagtaaccc acccaccgaa gcccacgacg
1921 actcccgaac ccaaatgtcc ggaggattgg ggcgccagca gtagaacaag cttgtgtttc
1981 aagctgtatg caaaaggaaa acatgagaag aaaacgtggt ttgaatctcg agatttttgt
2041 cgagctctgg gtggagactt agctagcatc aataacaaag aggaacagca aacaatatgg
2101 cgattaataa cagctagtgg aagctaccac aaactgtttt ggttgggatt gacatatgga
2161 agcccttcag aaggttttac ttggagtgat ggttctcctg tttcatatga aactgggct
2221 tatggagaac ctaataatta tcaaaatgtt gaatactgtg gtgagctgaa aggtgaccct
2281 actatgtctt ggaatgatat taattgtgaa caccttaaca actggatttg ccagatacaa
2341 aaaggacaaa caccaaaacc tgagccaaca ccagctcctc aagacaatcc accagttact
2401 gaagatgggt gggttattta caaagactac cagtattatt tcagcaaaga gaaggaaacc
2461 atggacaatg cgcgagcgtt ttgcaagagg aattttggtg atcttgtttc tattcaaagt
2521 gaaagtgaaa agaagtttct atggaaatat gtaaacagaa atgatgcaca gtctgcatat
2581 tttattggtt tattgatcag cttggataaa aagtttgctt ggatggatgg aagcaaagtg
2641 gattacgtgt cttgggccac aggtgaaccc aattttgcaa atgaagatga aaactgtgtg
2701 accatgtatt caaattcagg gttttggaat gacattaact gtggctatcc aaacgccttc
2761 atttgccagc gacataacag tagtatcaat gctaccacag ttatgcctac catgcccctcg
2821 gtcccatcag ggtgcaagga aggttggaat ttctacagca acaagtgttt caaaatcttt
2881 ggatttatgg aagaagaaag aaaaaattgg caagaggcac gaaaagcttg tataggcttt
2941 ggagggaatc tggtctccat acaaaatgaa aaagagcaag catttcttac ctatcacatg
3001 aaggactcca ctttcagtgc ctggactggg ctgaatgatg tcaattcaga acacacgttc
3061 ctttggacgg atggacgagg agtccattac acaaactggg ggaaaggtta ccctggtgga
3121 agaagaagca gtctttctta tgaagatgct gactgtgttg ttattattgg aggtgcatca
3181 aatgaagcag gaaaatggaa ggatgatacc tgcgacagta aacgaggcta catatgccag
3241 acacgatccg acccttcctt gactaatcct ccagcaacga ttcaaacaga tggctttgtt
3301 aaatatggca aaagcagcta ttcactcatg agacaaaaat ttcaatggca tgaagcggag
3361 acatactgca agcttcacaa ttcccttata gccagcattc tggatccta cagtaatgca
3421 tttgcgtggc tgcagatgga acatctaat gaacgtgtgt ggatcgccct gaacagtaac
3481 ttgactgata atcaatacac ttggactgat aagtggaggg tgaggtacac taactgggct
3541 gctgatgagc ccaaattgaa atcagcatgt gtttatctgg atcttgatgg ctactggaag
3601 acagcacatt gcaatgaaag tttttacttt ctctgtaaaa gatcagatga atccctgct
3661 actgaacccc cacaactgcc tggcagatgc ccggagtcag atcacacagc atggattcct
```

-continued

```
3721 ttccatggtc actgttacta tattgagtcc tcatatacaa gaaactgggg ccaagcttct
3781 ctggaatgtc ttcgaatggg ttcctctctg gtttccattg aaagtgctgc agaatccagt
3841 tttctgtcat atcgggttga gccacttaaa agtaaaacca atttttggat aggattgttc
3901 agaaatgttg aagggacgtg gctgtggata aataacagtc cggtctcctt tgtcaactgg
3961 aacacaggag atccctctgg tgaacggaat gattgtgtag ctttacatgc gtcttctggg
4021 ttttggagta atattcactg ttcatcctac aaaggatata tttgtaaaag accaaaaatt
4081 attgatgcta aacctactca tgaattactt acaacaaaag ctgacacaag gaagatggac
4141 ccttctaaac cgtcttccaa cgtggccgga gtagtcatca ttgtgatcct cctgattta
4201 acgggtgctg gccttgccgc ctatttcttt tataagaaaa gacgtgtgca cctacctcaa
4261 gagggcgcct ttgaaaacac tctgtatttt aacagtcagt caagcccagg aactagtgat
4321 atgaaagatc tcgtgggcaa tattgaacag aatgaacact cggtcatcta g
```
//

Human MRC1 amino acid sequence (SEQ ID NO:4, NCBI Accession: NP_002429)

```
   1 mrlplllvfa svipgavlll dtrqfliyne dhkrcvdays psavqtaacn qdaesqkfrw
  61 vsesqimsva fklclgvpsk tdwvaitlya cdsksefqkw eckndtllgi kgedlffnyg
 121 nrqeknimly kgsglwsrwk iygttdnlcs rgyeamytll gnangatcaf pfkfenkwya
 181 dctsagrsdg wlwcgtttdy dtdklfgycp lkfegseslw nkdpltsysy qinsksaltw
 241 hgarkscqqg naellsitei heqtyltglt ssltsglwig lnslsfnsgw qwsdrspfry
 301 lnwlpgspsa epgkscvsln pgknakwenl ecvqklgyic kkgnttlnsf vipsesdvpt
 361 hcpsqwwpya ghcykihrde kkiqrdaltt crkeggdlts ihtieeldfi isqlgyepnd
 421 elwiglndik iqmyfewsdg tpvtftkwlr gepshennrq edcvvmkgkd gywadrgcew
 481 plgyickmks rsqgpeivev ekgcrkgwkk hhfycymigh tlstfaeanq tcnnenaylt
 541 tiedryeqaf ltsfvglrpe kyfwtglsdi qtkgtfqwti eeevrfthwn sdmpgrkpgc
 601 vamrtgiagg lwdvlkcdek akfvckhwae gvthppkptt tpepkcpedw gassrtslcf
 661 klyakgkhek ktwfesrdfc ralggdlasi nnkeeqqtiw rlitasgsyh klfwlgltyg
 721 spsegftwsd gspvsyenwa ygepnnycin veycgelkgd ptmswndine hlnnwicgiq
 781 kgqtpkpept papqdnppvt edgwviykdy qyyfskeket mdnarafckr nfgdlvsiqs
 841 esekkflwky vnrndaqsay figllisldk kfawmdgskv dyvswatgep nfanedencv
 901 tmysnsgfwn dincgypnaf icqrhnssin attvmptmps vpsgckegwn fysnkcfkif
 961 gfmeeerknw qearkacigf ggnlvsigne keqafltyhm kdstfsawtg lndvnsehtf
1021 lwtdgrgvhy tnwgkgypgg rrsslsyeda dcvviiggas neagkwmddt cdskrgyicq
1081 trsdpsltnp patiqtdgfv kygkssyslm rqkfqwheae tycklhnsli asildpysna
1141 fawlqmetsn ervwialnsn ltdnqytwtd kwrvrytnwa adepklksac vyldldgywk
1201 tahcnesfyf lckrsdeipa teppqlpgrc pesdhtawip fhghcyyies sytrnwgqas
1261 leclrmgssl vsiesaaess flsyrveplk sktnfwiglf rnvegtwlwi nnspvsfvnw
1321 ntgdpsgern dcvalhassg fwsnihcssy kgyickrpki idakpthell ttkadtrkmd
1381 pskpssnvag vviivillil tgaglaayff ykkrrvhlpq egafentlyf nsgsspgtsd
1441 mkdlvgnieq nehsvi
```
//

Nucleic Acids, Vectors and Host Cells

The disclosure features isolated and/or recombinant (including, e.g., essentially pure) nucleic acid molecules comprising nucleic acid sequences which encode MRC1. The nucleic acid molecules include a 5' region wherein one or more codon of the nucleic acid sequence encoding wild type MRC1 has been replaced with a common codon.

Nucleic acid molecules referred to herein as "isolated" are nucleic acid molecules which have been separated away from the nucleic acids of the genomic DNA or cellular RNA of their source of origin (e.g., as it exists in cells or in a mixture of nucleic acids such as a library), and include nucleic acid molecules obtained by methods described herein or other suitable methods, including nucleic acid molecules produced by chemical synthesis, by combinations of biological and chemical methods, and recombinant nucleic acid molecules which are isolated.

In another aspect, the disclosure features host cells and vectors (e.g., recombinant expression vectors) containing the nucleic acids described herein.

Prokaryotic or eukaryotic host cells may be used. The terms "cell" and "recombinant cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic, e.g., bacterial cells such as $E.$ $coli$, or eukaryotic, e.g., insect cells, yeast, or preferably mammalian cells (e.g., cultured cell or a cell line). Other suitable host cells are known to those skilled in the art.

In some embodiments, the host cells do not express an Fc receptor. An Fc receptor is a protein found on the surface of certain cells that binds specifically to the Fc (Fragment, crystallizable) region of an antibody. Different types of Fc receptors, classified based on the type of antibody that they recognize, include, e.g., Fc-gamma receptors (FcγR), Fc-alpha receptors (FcαR), and Fc-epsilon receptors (FcεR), which can bind to IgG, IgA, and IgE, respectively.

In another aspect, the disclosure features a vector, e.g., a recombinant expression vector. The recombinant expression vectors can be designed for expression of MRC1, or functional portion thereof, in prokaryotic or eukaryotic cells. For example, MRC1 can be expressed in $E.$ $coli$, insect cells (e.g., using baculovirus expression vectors), yeast cells or mammalian cells. Alternatively, the recombinant expression vector can be transcribed and translated in vitro, for example using T7 promoter regulatory sequences and T7 polymerase.

In addition to the nucleic acid sequence encoding MRC1, the vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Kits and Pharmaceutical Compositions

The cells described herein can be provided in a kit. The kit includes (a) a cell or a plurality of cells described herein, and (b) informational material. The information material can be descriptive, instructional, marketing or other material that relates to the methods described herein and/or use of the cells described herein for the methods described herein. In one embodiment, the informational material can include instructions for, e.g., detecting anti-glucerebrosidase antibody in a sample, identifying a suitable subject for a glucerebrosidase replacement therapy, and/or selecting a treatment for a subject with Gaucher disease. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

The kit can include one or more containers. In some embodiments, the kit contains separate containers, dividers or compartments for the cells and informational material. For example, the cells can be contained in a bottle or vial, and the informational material can be contained in a plastic sleeve or packet. In other embodiments, the separate elements of the kit are contained within a single, undivided container. For example, the cells are contained in a bottle or vial that has attached thereto the informational material in the form of a label. In some embodiments, the kit includes a plurality (e.g., a pack) of individual containers. The containers of the kits can be air tight and/or waterproof.

Optionally, the composition of kit can include other elements, such as a solvent or buffer, cell culture medium, a stabilizer or a preservative, a labeling or detecting reagent, an anti-GCB antibody, e.g., as a positive control. Alternatively, the other elements can be included in the kit, but in different compositions or containers than the cells.

Gaucher Disease

Cells and methods described herein can be used to select a treatment for a subject with Gaucher disease. Gaucher disease is the most common of the lysosomal storage diseases. It is caused by a hereditary deficiency of the enzyme glucocerebrosidase (also known as acid β-glucosidase). The enzyme acts on a fatty substance glucocerebroside (also known as glucosylceramide). When the enzyme is defective, the substance accumulates, particularly in cells of the mononuclear cell lineage. Fatty material can collect in the spleen, liver, kidneys, lungs, brain and bone marrow. Symptoms may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the white of the eye (sclera). Persons affected most seriously may also be more susceptible to infection. The disease is caused by a recessive gene on chromosome 1 and affects both males and females.

Gaucher disease has three common clinical subtypes:

Type I (or non-neuropathic type) is the most common form of the disease, occurring in approximately 1 in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leucopenia. The brain is not affected, but there may be lung and, rarely, kidney impairment. Patients in this group usually bruise easily (due to low levels of platelets) and experience fatigue due to low numbers of red blood cells. Depending on disease onset and severity, type 1 patients may live well into adulthood. Many patients have a mild form of the disease or may not show any symptoms. In some embodiments, the methods and compositions described herein are used to treat type I Gaucher disease.

Type II (or acute infantile neuropathic Gaucher disease) typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

Type III (the chronic neuropathic form) can begin at any time in childhood or even in adulthood, and occurs in approximately 1 in 100,000 live births. It is characterized by slowly progressive but milder neurologic symptoms compared to the acute or type 2 version. Major symptoms include an enlarged spleen and/or liver, seizures, poor coordination, skeletal irregularities, eye movement disorders, blood disorders including anemia and respiratory problems. Patients often live into their early teen years and adulthood.
Velaglucerase Cells and methods described herein can be used to identify a subject suitable for a GCB enzyme replacement therapy, e.g., treatment with velaglucerase.

Velaglucerase can, for example, be administered by injection, intravenously, intraarterially, subdermally, intraperitoneally, intramuscularly, or subcutaneously. Preferably velaglucerase is administered invtravenously.

Velaglucerase is administered at doses between (and including) 2.5 U/kg and 60 U/kg of subject body weight (e.g., 15 U/kg, 30 U/kg, 45 U/kg, or 60 U/kg).

Velaglucerase can be administered at a rate of 1 U/kg/minute. The dose of velaglucerase can be administered to the subject every other week.

Velaglucerase can be administered at a dose of about 15 U/kg to about 60 U/kg of subject body weight (e.g. about 30 U/kg to about 60 U/kg, e.g., about 15 U/kg, 30 U/kg, 45 U/kg, or 60 U/kg), at a dose equal to or below about 22.5 U/kg, at a dose between about 22.5 U/kg and about 37.5 U/kg, at a dose between about 37.5 U/kg and about 52.5 U/kg, or at a dose equal to or above about 52.5 U/kg. In some embodiments, velaglucerase can be administered at a dose of 2.5 U/kg to 60 U/kg. In some embodiments, the velaglucerase can be administered every other week by intravenous infusion. In other embodiments, the velaglucerase can be administered every week by intravenous infusion. In some embodiments, the velaglucerase can be administered three times a week by intravenous infusion, e.g., at a dose of about 2.5 U/kg.

In some embodiments, the infusion of the dose (e.g., a dose of about 15 U/kg to 60 U/kg, a dose of about 30 U/kg to 60 U/kg, a dose equal to or below about 22.5 U/kg, a dose between about 22.5 and about 37.5 U/kg, a dose between about 37.5 and about 52.5 U/kg, a dose equal to or above about 52.5 U/kg, or a dose of about 15 U/kg, 30 U/kg, 45 U/kg, or 60 U/kg) occurs over about 60 minutes.
Alternative Therapy The administration of velaglucerase (with or without the additional agent) can be used as an alternative treatment, e.g., for subjects who were previously treated with another therapy (i.e., a therapy other than velaglucerase, e.g., imiglucerase, alglucerase, isofagomine tartrate, miglustat, or Genz112638). For example, a subject who is undergoing treatment for Gaucher disease with another therapy can be transferred to treatment with velaglucerase, e.g., if the presence of antibodies (e.g., neutralizing antibodies) to the other therapy has been detected in the subject. For example, a subject who is undergoing treatment for Gaucher disease with imiglucerase can be transferred to treatment with velaglucerase, e.g., velaglucerase can be administered at the same dose and with the same frequency at which the imiglucerase was administered.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Cloning and Generation of Cell Lines Stably Transfected with Human Macrophage Mannose Receptor C Type 1 (MRC1)

Example 1.1

Cloning of MRC1 Gene and Construction of Human MRC1 Expression Vector

The human MRC1 gene was cloned from a human liver cDNA library by polymerase chain reaction (PCR) using the following oligonucleotides: 5'-TTACGCGTCCACCAT-GAGGCTACCCCTGCTC-3' (forward primer with MluI site, SEQ ID NO: 5) and 5'-TTAATTAACTAGATGAC-CGAGTGT-3' (reverse primer with PacI site, SEQ ID NO: 6). The PCR product was digested with restriction enzymes and inserted into the pX vector (Shire) under a collagen promoter.

The survival of *E. coli* from purported MRC1 gene or gene product toxicity resulted from inversion of part of the 5' region of the cDNA during cloning (Razin S V et al., *J. Mol. Biol.* (2001) 307(2):481-486). To overcome this difficulty, the MRC1 gene sequence was analyzed and the region that caused inversion of a portion of the gene (5' end of the gene) was identified. Next, the 5' region of MRC1 gene (nucleotides 1-2067) was codon optimized as shown in FIGS. 1A-1E (retaining the native protein sequence) and synthesized (Bio Basic Inc., Markham, ON, CA). This codon optimized portion was inserted to replace the inverted section of the MRC1 gene, creating pX-MRC1. The resulting MRC1 gene was verified by sequencing.

Example 1.2

Generation of Cell Line Stably Transfected with Human MRC1

Cell line MRC1-18 is derived from the human fibrosarcoma cell line HT1080, and is stably-transfected with human MRC1 (the macrophage mannose receptor). HT1080 (saf) cells were transfected with pX-MRC1 by electroporation and immediately plated into 96-well plates with Cloning Media using limiting dilution cloning. Stable clones were selected using Cloning Media containing 0.4 mg/mL G418. MRC1 expression was analyzed using FITC anti-MRC1 staining and analyzed by guava fluorescence shift. 39 clones were analyzed and several clones showed high levels of MRC1 expression. The top 4 clones were retained along with some clones expressing lower levels of MRC1 for comparison using FACS Canto fluorescence shift. Additionally, MRC1-18 clone was verified by immunostaining and flow cytometry to be negative for expression of Fc (gamma) receptors. MRC1-18 cells were maintained in CD media supplemented with 0.5 mg/mL G418.

Example 2

Identification of MRC1 Expression in HT1080(Saf) Stable Transfectants

Figure 2A:
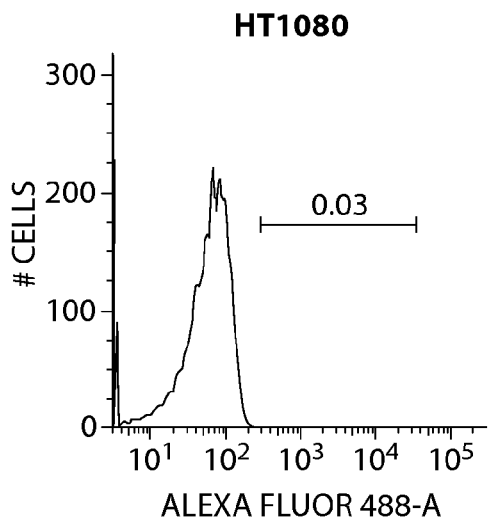
FIGS. 2A-2J depict FACS analyses of the expression of MRC1 in untransfected HT1080 cells, stable pool of transfected cells, and stable transfected clones.
Figure 2B:
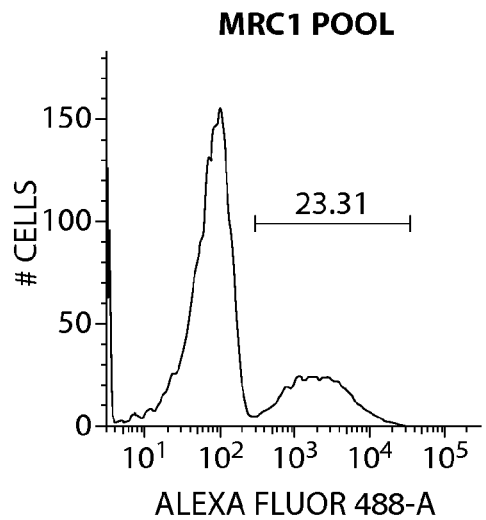
Figure 2C:
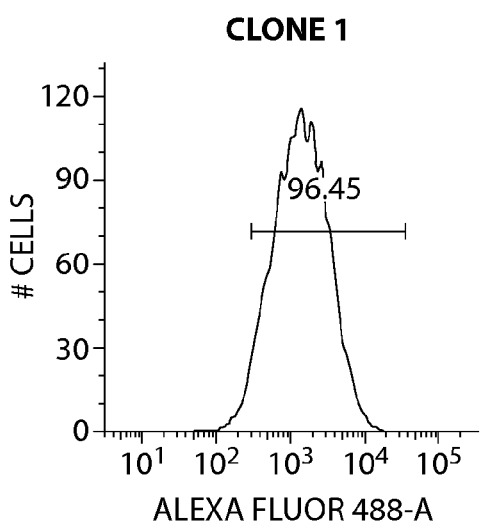
Figure 2D:
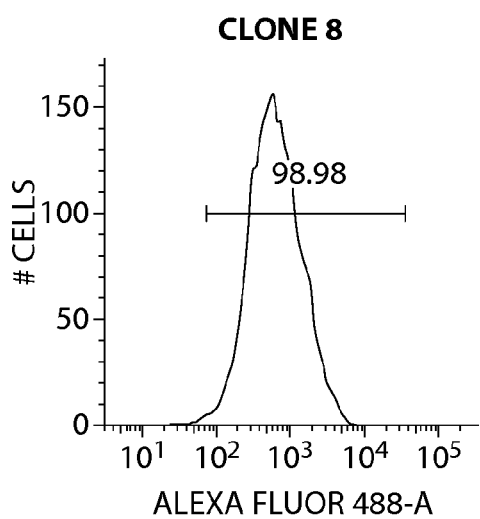
Figure 2E:
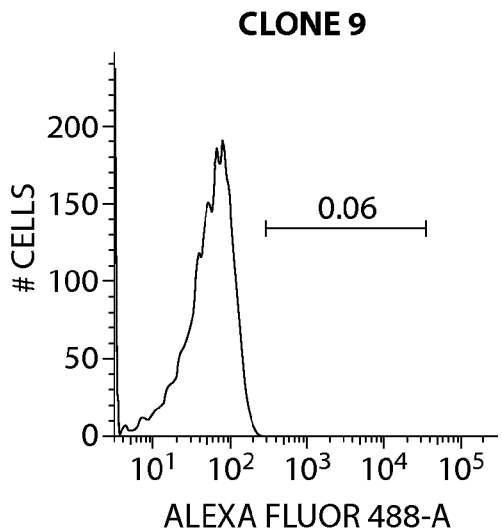
Figure 2F:
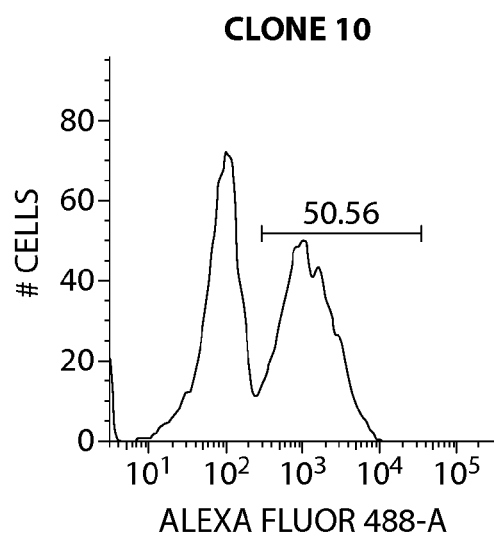
Figure 2G:
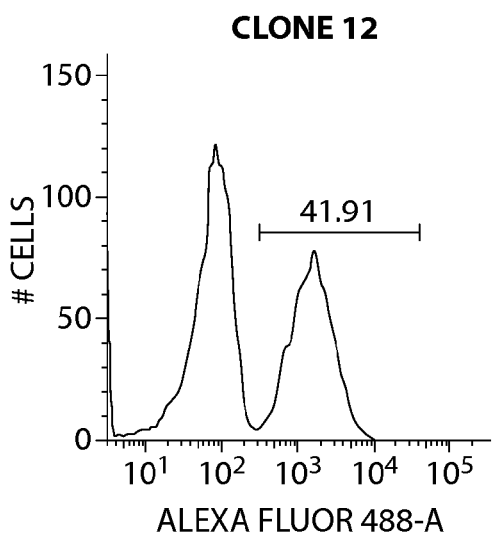
Figure 2H:
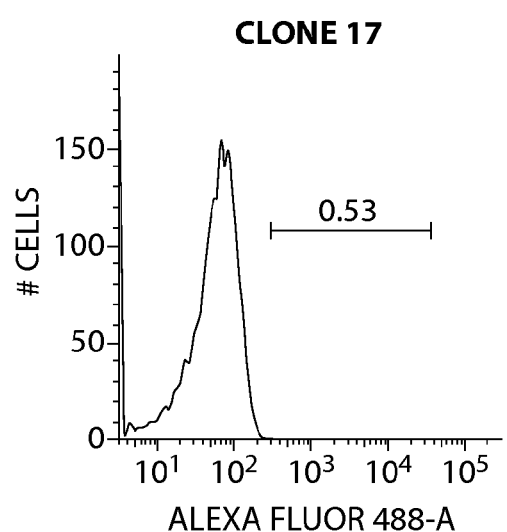
Figure 2I:
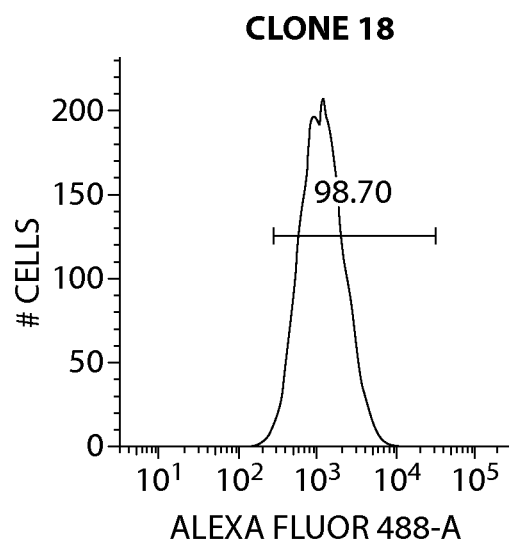
Figure 2J:
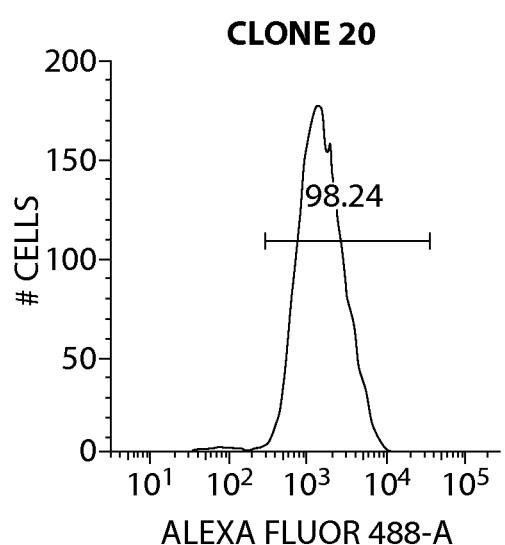
Figure 3A:
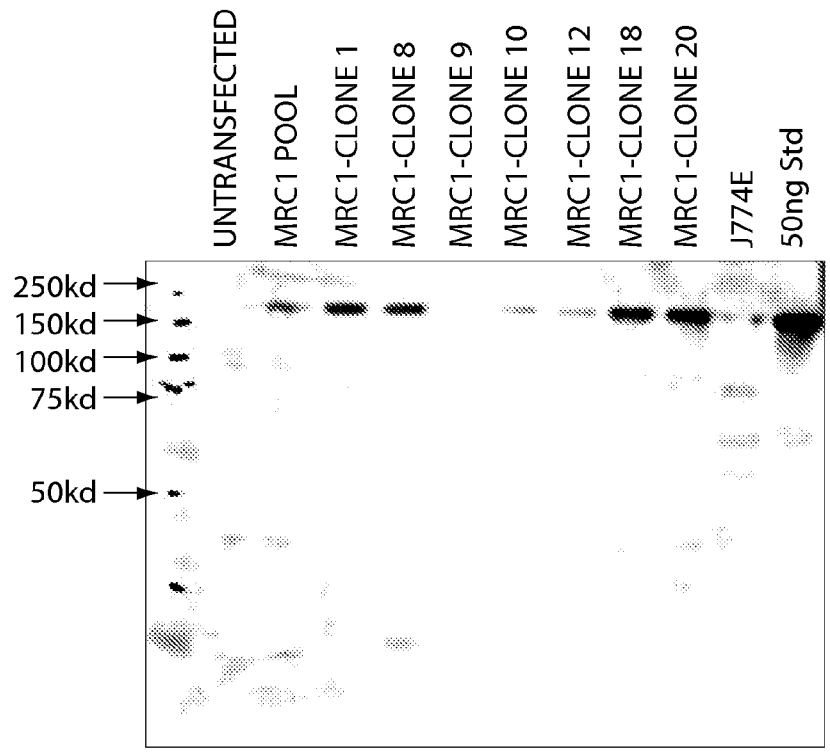
FIG. 3A depicts a Western analysis of MRC1 expression in the transfected cells.
Figure 3B:
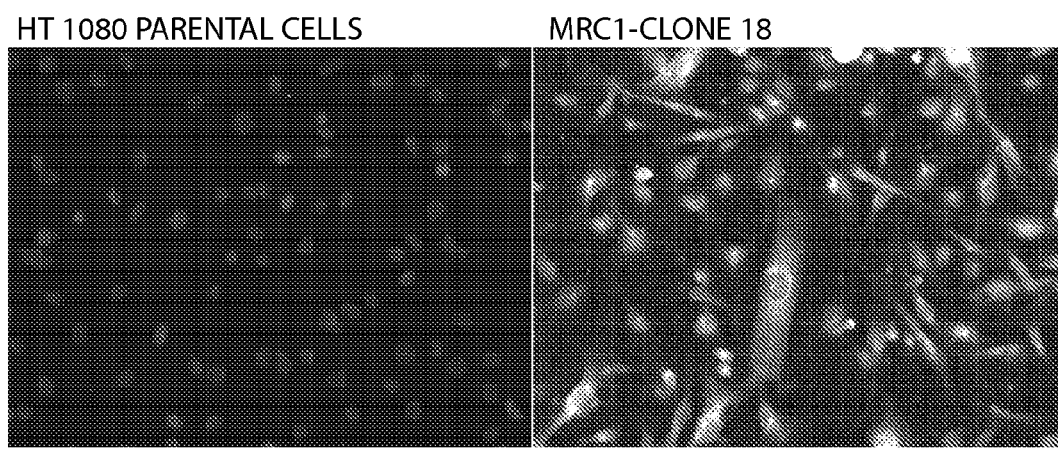
FIG. 3B depicts an immunohistochemistry analysis of MRC1 expression in MRC1-18 cells.

Stable MRC1-expressing clones, as well as a stable pool of transfected cells which had not been subcloned, were expanded in CD Media containing 0.4 mg/ml G418. To determine expression of MRC1, $1 \times 10^6$ cells per sample were incubated in 1 ml CD media with 20 μl of FITC conjugated Mouse anti-human MRC1 antibody (BD Biosciences Cat #551135) for 20 minutes. Cells were rinsed 2 times with 1 ml PBS, resuspended in 100 μl CD media, and analyzed on a BD Biosciences FACSCanto Flow Cytometer. Results are shown in FIGS. 2A-2J. A subpopulation of MRC1 positive cells with a Relative Fluorescence Intensity (RFI) approximately 1.5 logs above the background was observed in the transfected pool (FIG. 2B) compared to untransfected HT1080 cells (FIG. 2A). This MRC1 positive population was enriched after cloning (FIGS. 2C-2J). Western blot analysis of MRC1 expression by the transfectants revealed a single protein band at the expected size of 160-170 kDa (FIG. 3A). Immunohistochemical analysis of MRC1-18 cells using a FITC conjugated antibody against MRC1 (FIG. 3B) shows expression of MRC1 in HT1080 cells transfected with MRC1 but not in the parent cell line.

Figure 4A:
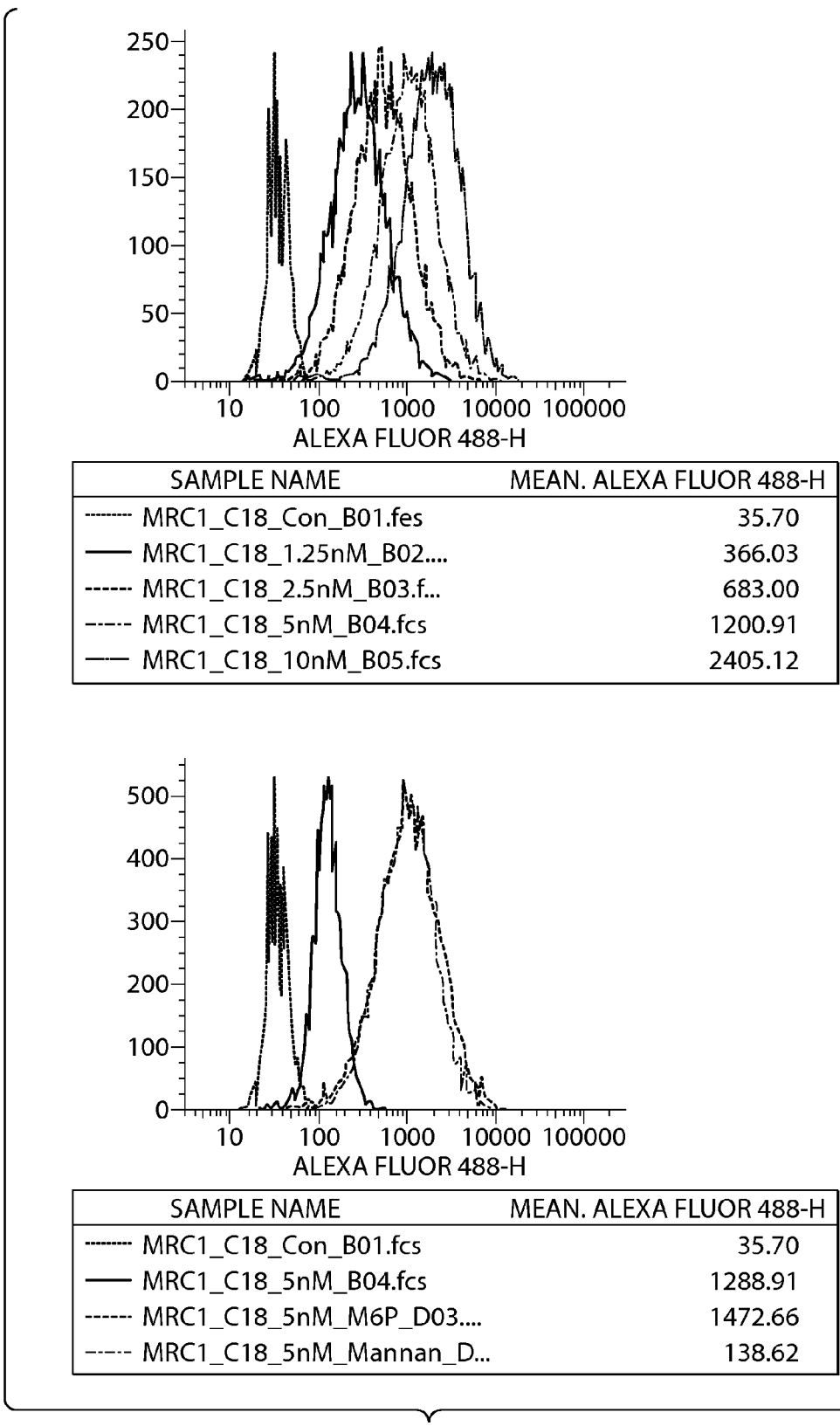
FIG. 4A depicts the dose-dependent uptake of rhGCB in MRC1-18 cells.
Figure 4B:
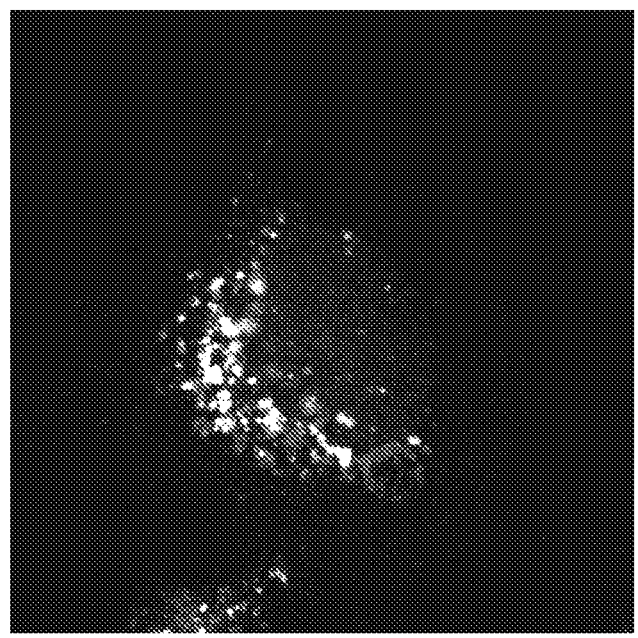
FIG. 4B depicts an immunohistochemistry analysis of rhGCB internalization in MRC1-18 cells.

To verify that MRC1-18 cells are functional, different doses of rhGCB were tested for uptake in the cells. As shown in FIG. 4A, rhGCB is taken up by MRC1-18 in a dose-dependent manner and the uptake is inhibited by mannan but not by M6P, suggesting that internalization of rhGCB is through the MRC1 receptor. As shown in FIG. 4B, immunohistochemistry indicates that rhGCB is internalized and localizes to the lysosome, confirming that trafficking of rhGCB in MRC1-18 cells occurs in a normal fashion.

Example 3

Cell-Based Antibody Inhibition of MMR-Mediated Enzyme Uptake

Inhibition of enzyme uptake by anti-velaglucerase alfa or anti-imiglucerase antibodies was tested using a cell-based assay that detects and quantifies antibodies that interfere with macrophage mannose receptor (MMR) mediated velaglucerase alfa or imiglucerase uptake. The method is based on quantification of fluorescently labeled velaglucerase alfa or imiglucerase which is internalized by MRC1-18 cells under defined conditions. MRC1-18 is a cell line engineered at Shire HGT from HT1080 cells that were stably-transfected with the human macrophage mannose receptor C, type 1.

Briefly, anti-velaglucerase alfa or anti-imiglucerase antibody positive serum samples were pre-incubated with MRC1 18 cells in culture media in flat bottom, 96-well plates at 37° C. for 15 minutes. Pooled normal human serum (NHS) was used as negative control. Sheep polyclonal antibodies known to inhibit velaglucerase alfa and imiglucerase uptake as well as mannan, the MMR-specific ligand were used as positive controls to block enzyme uptake.

Following preincubation, Alexa Fluor 488 labeled velaglucerase alfa or imiglucerase was added, and incubated at 37° C. for an additional 2 hours. A calibration curve consisting of incubation of Alexa Fluor 488 labeled enzyme with MRC1-18 cells was included in each experiment. After incubation, media was removed by centrifugation, cells were treated with trypsin-EDTA for 3 minutes to remove surface bound enzyme, and finally the reaction pH was returned to neutral pH by addition of an equal volume of culture media. Cells were washed once and resuspended using phosphate buffered saline containing 0.5% BSA. Cells were analyzed using a Becton Dickinson FACS Canto II instrument calibrated before each analysis using the instrument's cytometer setup and tracking beads.

The results were analyzed with the instrument's FlowJo software, and the mean fluorescence intensity (MFI) for each sample was recorded. The adjusted MFI was calculated by subtracting the background MFI from sample wells containing no enzyme from each unknown and control sample MFI. Inhibition of enzyme uptake by patient serum samples was estimated relative to the NHS control according to the following equation:

% Inhibition=[1−[Adjusted MFI of test sample/Adjusted MFI of NHS]]×100

The assay cut point was determined by analysis of 25 individual sera collected from treatment-naïve Gaucher patients. Each serum was tested on four separate days for a total of 100 values and the positive cut point was defined as inhibition greater than the mean of these values plus 1.645 standard deviations.

What is claimed:

1. A method of measuring cellular uptake of glucocerebrosidase (GCB) into a mammalian cell, the method comprising:
    contacting a mammalian cell that stably expresses on its surface mannose receptor, C type 1 (MRC1) with GCB; and
    measuring the amount of GCB in the cell,
    wherein the cell comprises a nucleic acid molecule comprising a nucleic acid sequence encoding a MRC1 polypeptide having an amino acid sequence that is at least 99% identical to SEQ ID NO:4, wherein the nucleic acid sequence encoding the MRC1 polypeptide comprises optimized codons so that at least 15% of the nucleic acid residues within positions 1 to 2067 of the nucleic acid sequence are different from positions 1 to 2067 of SEQ ID NO: 1, and
    wherein the optimized codon refers to the following codons: Ala (gcc); Arg (aga); Asn (aac); Asp (gac); Cys (ugc); Gln (cag); Gly (ggc); His (cac); Ile (auc); Leu (cug); Lys (aag); Pro (ccc); Phe (uuc); Ser (agc); Thr (acc); Tyr (uac); Glu (gag); and Val (gug).

2. The method of claim 1, wherein at least about 450 residues within positions 1 to 2067 of the nucleic acid sequence encoding the MRC1 polypeptide are different from positions 1 to 2067 of SEQ ID NO:1.

3. The method of claim 1, wherein the nucleic acid sequence encoding the MRC1 polypeptide comprises at least about 350 codons that are optimized codons.

4. The method of claim 1, wherein at least 20% of the nucleic acid residues within positions 1 to 2067 of the nucleic acid sequence encoding the MRC1 polypeptide are different from positions 1 to 2067 of SEQ ID NO:1.

5. The method of claim 1, wherein at least about 50% of the codons within positions 1 to 2067 of the nucleic acid sequence encoding the MRC1 polypeptide are optimized codons.

6. The method of claim 1, wherein the 5' region of the nucleic acid sequence encoding the MRC1 polypeptide comprises a nucleic acid sequence which is at least about 85% identical to the nucleic acid sequence of SEQ ID NO:2, SEQ ID NO:3, or SEQ ID NO:7.

7. A method of measuring cellular uptake of glucocerebrosidase (GCB) into a mammalian cell, the method comprising:
contacting a mammalian cell that stably expresses on its surface mannose receptor, C type 1 (MRC1) with GCB; and
measuring the amount of GCB in the cell,
wherein the cell comprises a nucleic acid molecule comprising a nucleic acid sequence encoding a MRC1 polypeptide having an amino acid sequence that is at least 99% identical to SEQ ID NO:4, wherein the 5' region of the nucleic acid sequence encoding the MRC1 polypeptide comprises nucleic acid sequence selected from the group consisting of SEQ ID NO:2, SEQ ID NO:3, and SEQ ID NO:7.

8. The method of claim 1, wherein the 3' region of the nucleic acid sequence encoding the MRC1 polypeptide comprises residues 2088 to 4371 of SEQ ID NO:1.

9. The method of claim 1, wherein the 3' region of the nucleic acid sequence encoding the MRC1 polypeptide comprises the sequence which is at least about 50% identical to residues 2088 to 4371 of SEQ ID NO:1.

10. The method of claim 1, wherein the 3' region of the nucleic acid sequence encoding the MRC1 polypeptide comprises at least one optimized codon.

11. The method of claim 1, wherein at least about 10% of the codons of the 3' region of the nucleic acid sequence encoding the MRC1 polypeptide are optimized codons.

12. The method of claim 1, wherein at least about 100 codons of the 3' region of the nucleic acid sequence encoding the MRC1 polypeptide are optimized codons.

13. The method of claim 1, wherein the cell is a human cell.

14. The method of claim 1, wherein the cell is an HT-1080 cell.

15. The method of claim 1, wherein the cell does not express an Fc receptor.

16. The method of claim 1, wherein the GCB is velaglucerase or imiglucerase.

17. The method of claim 16, wherein the amount of uptake of velaglucerase is compared to the amount of uptake of imiglucerase.

18. The method of claim 1, wherein the amount of GCB is measured about 2 hours after the cell has been contacted with the GCB.

19. The method of claim 1, wherein the GCB is labeled.

20. The method of claim 1, wherein the amount of uptake is measured by measuring GCB enzymatic activity in the cell or intracellular GCB protein levels.

21. The method of claim 1, wherein the cell is contacted with GCB in the absence of one or more of: mannose-6-phosphate, mannan, and calcium.

22. The method of claim 1, wherein the cell is washed one or more times prior to the measuring step.

23. The method of claim 1, wherein the cell is contacted with GCB in the presence of one or more of: mannose-6-phosphate (M6P), mannan, and calcium.

24. The method of claim 21, wherein the amount of uptake is compared to a reference standard, wherein the reference standard is the measured amount of uptake in the presence of one or more of: mannose-6-phosphate, mannan, and calcium.

25. The method of claim 23, wherein the amount of uptake is compared to a reference standard, wherein the reference standard is the measured amount of uptake in the absence of one or more of: mannose-6-phosphate, mannan, and calcium.

26. The method of claim 7, wherein the 3' region of the nucleic acid sequence encoding the MRC1 polypeptide comprises residues 2088 to 4371 of SEQ ID NO:1.

* * * * *

UNITED STATES PATENT AND TRADEMARK OFFICE
CERTIFICATE OF CORRECTION

PATENT NO. : 9,453,847 B2
APPLICATION NO. : 13/811122
DATED : September 27, 2016
INVENTOR(S) : Juan A. Ruiz et al.

It is certified that error appears in the above-identified patent and that said Letters Patent is hereby corrected as shown below:

On the Title Page

Item (75), replace inventor "PAN LUYING, Newton, MA (US)" with "LUYING PAN, Newton, MA (US)".

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*